United States Patent
Zucchi et al.

(10) Patent No.: US 11,566,070 B2
(45) Date of Patent: Jan. 31, 2023

(54) AGENTS THAT MODULATE TMEM230 AS ANGIOGENESIS REGULATORS AND THAT DETECT TMEM230 AS MARKERS OF METASTASIS

(71) Applicant: CONSIGLIO NAZIONALE DELLE RICERCHE, Rome (IT)

(72) Inventors: Ileana Zucchi, Rome (IT); Rolland Alvons Reinbold, Rome (IT)

(73) Assignee: CONSIGLIO NAZIONALE DELLE RICERCHE, Rome (IT)

( * ) Notice: Subject to any disclaimer, the term of this patent is extended or adjusted under 35 U.S.C. 154(b) by 0 days.

(21) Appl. No.: 16/482,455

(22) PCT Filed: Feb. 5, 2018

(86) PCT No.: PCT/IB2018/050708
§ 371 (c)(1),
(2) Date: Jul. 31, 2019

(87) PCT Pub. No.: WO2018/142362
PCT Pub. Date: Aug. 9, 2018

(65) Prior Publication Data
US 2020/0247882 A1 Aug. 6, 2020

(30) Foreign Application Priority Data
Feb. 6, 2017 (IT) .................. 102017000012604

(51) Int. Cl.
| | | |
|---|---|---|
| *C12N 15/11* | (2006.01) | |
| *C07K 16/28* | (2006.01) | |
| *C12N 15/113* | (2010.01) | |
| *G01N 33/574* | (2006.01) | |

(52) U.S. Cl.
CPC ............ *C07K 16/28* (2013.01); *C12N 15/113* (2013.01); *G01N 33/57488* (2013.01); *C12N 2310/315* (2013.01); *C12N 2310/321* (2013.01)

(58) Field of Classification Search
CPC ............ C12N 15/113; C12N 2310/315; C12N 2310/321; G01N 33/574
See application file for complete search history.

(56) References Cited

U.S. PATENT DOCUMENTS

| | | | | |
|---|---|---|---|---|
| 2010/0311815 A1* | 12/2010 | Chinnaiyan | .......... | C12Q 1/6886 514/44 R |
| 2015/0037299 A1* | 2/2015 | Brodie | .................... | A61K 35/28 435/7.1 |

FOREIGN PATENT DOCUMENTS

| | | |
|---|---|---|
| EP | 2 806 274 | 11/2014 |

OTHER PUBLICATIONS

Huang et al, miRNA goes nuclear, RNA Biology, 2012, 9, 3: 269-273 (Year: 2012).*
Mitra et al, Nanoparticle-mediated miR200-b delivery for the treatment of diabetic retinopathy, Journal of Controlled Release, Jun. 2016, 236: 31-37 (Year: 2016).*
Vizcaino et al, Sp1 transcription factor: Along-standing target in cancer chemotherapy, Pharmacology & Therapeutics, 2015, 152: 111-124 (Year: 2015).*
Yang et al, miR-203 protects microglia mediated brain injury by regulating inflammatory responses via feedback to MyD88 in ischemia, Molecular Immunology, 2015, 65: 293-301 (Year: 2015).*
Li et al, miR-134 inhibits epithelial to mesenchymal transition by targeting FOXM1 in non-small cell lung cancer cells, FEBS Letters, 2012, 586: 3761-3765 (Year: 2012).*
International Search Report and Written Opinion of the ISA for PCT/IB2018/050708, dated Apr. 18, 2018, 18 pages.
Deng et al., "Identification of TMEM230 mutations in familial Parkinson's disease", Nature Genetics, vol. 48, No. 7, Jul. 1, 2016, 9 pages.
Farrer et al., "TMEM230 is not a gene for Parkinson's disease", bioRxiv, Jan. 1, 2017, 10 pages.
Alfonso et al. "Why one-size-fits-all vaso-modulatory interventions fail to control glioma invasion: In silico insights" Sci Rep; Nov. 2016; 6: 37283.
Carmeliet & Jain "Molecular mechanisms and clinical applications of angiogenesis" Nature; May 2011; 473(7347): 298-307.
Carmeliet & Jain "Principles and mechanisms of vessel normalization for cancer and other angiobenic diseases" Nat Rev Drug Discov; Jun. 2011; 10(6): 417-427.
Carra et al. "Zebrafish Tmem230a cooperates with the Delta/Notch signaling pathway to modulate endothelial cell number in angiogenic vessels" J Cell Physiol; Feb. 2018; 233(2).
Cocola et al. "Transmembrane-230 protein as novel target for treatment of glioblastoma white matter tumor" Front Cell Neurosci; in review.
Fukumura et al. "Enhancing cancer immunotherapy using antiangiogenics: Opportunities and challenges" Nat Rev Clin Oncol; May 2018; 15(5): 325-340.
Goel et al. "Normalization of the vasculature for treatment of cancer and other diseases" Physiol Rev; Jul. 2011; 91(3): 1071-1121.
Huang et al. "Anti-angiogenesis or pro-angiogenesis for cancer treatment: Focus on drug distribution" Int J Clin Exp Med; Jun. 2015; 8(6): 8369-8376.
Jain "Normalizing tumor vasculature with anti-angiogenic therapy: A new paradigm for combination therapy" Nat Med; Sep. 2001; 7(9): 987-989.
Jain "Normalization of tumor vasculature: An emerging concept in antiangiogenic therapy" Science; Jan. 2005; 307(5706): 58-62.
Jain "Anti-angiogenesis strategies revisited: From starving tumors to alleviating hypoxia" Cancer Cell; Nov. 2014; 26(5): 605-622.

(Continued)

*Primary Examiner* — Ekaterina Poliakova-Georgantas
(74) *Attorney, Agent, or Firm* — Studebaker & Brackett PC

(57) ABSTRACT

The present invention relates to agents that modulate/regulate the activity of the protein TMEM230 for use in the therapeutic treatment of pathologies in which therapeutic regulation of angiogenesis is advisable or necessary.

10 Claims, 19 Drawing Sheets

Figure 1:
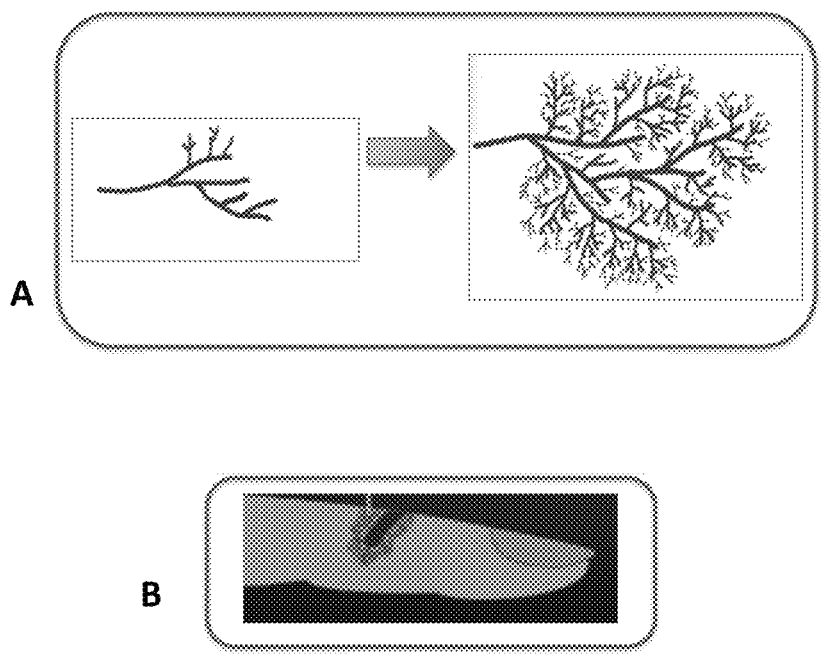

Specification includes a Sequence Listing.

(56) References Cited

OTHER PUBLICATIONS

Lupo et al. "Anti-angiogenic therapy in cancer: Downsides and new pivots for precision medicine" Front Pharmacol; Jan. 2017; 7: 519.
Ma & Waxman "Combination of antiangiogenesis with chemotherapy for more effective cancer treatment" Mol Cancer Ther; Dec. 2008; 7(12): 3670-3684.
Oronsky et al. "Beyond antiangiogenesis: Vascular modulation as an anticancer therapy—A review" Transl Oncol; Jun. 2012; 5(3): 133-140.
Rust et al. "Pro- and antiangiogenic therapies: Current status and clinical implications" FASEB J; Jan. 2019; 33(1): 34-48.
Schultz & MacKall "Driving CAR T cell translation forward" Sci Transl Med; Feb. 2019; 11(481): eaaw2127.
Khan & Kerbel "Improving immunotherapy outcomes with anti-angiogenic treatments and vice versa" Nat Rev Clin Oncol; May 2018; 15(5): 310-324.

\* cited by examiner a.  b.

TETon: system of transcriptional activation controlled by tetracycline
rtTA3: tetracyline transactivation factor
CMVtight: doxocycline responsive promoter OTHER TOOLS
- siRNAs
- Plasmids for the stable expression of TMEM230 sh based on the siRNA sequence (selectable for anitbiotic resistance)
- Plasmids for the stable expression of the fusion protein TMEM230iso2-GFP (selectable for antibiotic resistance)

SEQUENCE LISTING

```
<160> NUMBER OF SEQ ID NOS: 6

<210> SEQ ID NO 1
<211> LENGTH: 21
<212> TYPE: RNA
<213> ORGANISM: artificial sequence
<220> FEATURE:
<223> OTHER INFORMATION: siRNA for TMEM230 regulation

<400> SEQUENCE: 1
gaaacuauag cugaggacut t                                              21

<210> SEQ ID NO 2
<211> LENGTH: 21
<212> TYPE: RNA
<213> ORGANISM: artificial sequence
<220> FEATURE:
<223> OTHER INFORMATION: siRNA for TMEM230 regulation

<400> SEQUENCE: 2
aguccucagc uauaguuuct t                                              21

<210> SEQ ID NO 3
<211> LENGTH: 21
<212> TYPE: RNA
<213> ORGANISM: artificial sequence
<220> FEATURE:
<223> OTHER INFORMATION: siRNA for TMEM230 regulation

<400> SEQUENCE: 3
gguccuuccc aaagauguut t                                              21

<210> SEQ ID NO 4
<211> LENGTH: 21
<212> TYPE: RNA
<213> ORGANISM: artificial sequence
<220> FEATURE:
<223> OTHER INFORMATION: siRNA for TMEM230 regulation

<400> SEQUENCE: 4
aacaucuuug ggaaggacct t                                              21

<210> SEQ ID NO 5
<211> LENGTH: 21
<212> TYPE: RNA
<213> ORGANISM: Artificial Sequence
<220> FEATURE:
<223> OTHER INFORMATION: siRNA for TMEM230 regulation

<400> SEQUENCE: 5
gauguuaagu gaaccuacat t                                              21

<210> SEQ ID NO 6
<211> LENGTH: 21
<212> TYPE: RNA
<213> ORGANISM: artificial sequence
<220> FEATURE:
<223> OTHER INFORMATION: siRNA for TMEM230 regulation

<400> SEQUENCE: 6
uguagguuca cuuaacauct t                                              21
```

AGENTS THAT MODULATE TMEM230 AS ANGIOGENESIS REGULATORS AND THAT DETECT TMEM230 AS MARKERS OF METASTASIS

The present invention relates to agents that modulate/regulate the activity of the protein TMEM230 for use in the therapeutic treatment of diseases in which therapeutic angiogenesis regulation is advisable or necessary.

The present invention therefore relates to pharmaceutical compositions comprising one or more agents as defined above, more specifically agents that modulate/regulate the activity of the protein TMEM230 at expression level (transcription, translation) of the gene TMEM230 or at protein level (inhibition, mimetic peptides, etc.) and at least one pharmaceutically acceptable carrier for use in the therapeutic treatment of diseases in which therapeutic angiogenesis regulation is necessary.

The present invention also relates to the therapeutic treatment of pathologies in which therapeutic angiogenesis regulation is necessary by means of administration in therapeutically effective doses of one or more agents that regulate/modulate the activity of the protein TMEM230 as described above, or of pharmaceutical compositions containing same.

PRIOR ART

Vasculogenesis is the process responsible for the initial formation of blood vessels from progenitor cells. This is essential for the development of the primordial organs and is one of the fundamental processes associated with embryonic development. Embryonic development of the blood vessels includes the differentiation, migration and coalescence of the progenitor endothelial cells of mesodermal origin. After the rudimentary assembly of the blood cells, the endothelial cells (ECs) of arterial origin undergo a process of germination, which subsequently promotes branching and allows the generation of new vessels that form by germination from pre-existing vessels by means of a process referred to as angiogenesis. Angiogenesis is therefore a process of remodelling and of formation of new blood vessels from pre-existing vessels (FIG. 1A). Other than during embryonic development, this takes place in adults during the normal process of tissue homeostasis, or in pathological conditions, such as in the diseases known as macular degeneration, in vascular diseases, in tumour progression, and in the process of metastatisation, and it is necessary in tissue repair and regeneration processes following injury (FIG. 1B). The formation of new blood cells occurs also during tissue regeneration following ischaemic lesions or in chronic diseases such as diabetes. The network of blood vessels therefore undergoes constant remodelling in order to respond to the demands of the tissue.

As occurs in the process of embryonic vasculogenesis, when tissue lesions occur during tumour development, the endothelial cells receive stimuli that induce them to proliferate. The functional vessels contain endothelial cells that have a cobblestone-like regular polygonal morphology, which they maintain in a dormant state until they detect pro-angiogenic signals, which induce them to lose junctional cell-cell contacts and to activate proteases that degrade the surrounding basement membrane, allowing the ECs to change morphology, grow longer, and acquire the ability to become invasive and mobile. In the case of normal tissue homeostasis, the functional vessels are formed primarily by dormant endothelial cells (FIG. 2A) and only a small number of ECs are selected to drive the germination of new vessels in the surrounding tissue. These epithelial cells provided with motility are called tip cells (TCs), that is to say pointed cells, and are able to develop dynamic extensions, called filopodia, which are essential for migration (FIG. 2B). The dormant cells of the functional cells are instead called stalk cells (SCs) and, in contrast to tip cells, are able to maintain cell-cell contacts and provide an anchoring and structural support for the correct functioning of the vessels and for germination of tip cells (FIG. 2B). The sprouting process continues until the TC connects with adjacent vessels and fuses therewith by anastomosis (FIG. 2C). Once the connection has been established, the tip cells lose their mobile phenotype, the sprouting behaviour is suppressed, and the dormant phenotype is re-established (FIG. 2D). Whereas successive cycles of angiogenesis allow the further expansion of the vascular network, the lateral redistribution of the following junctional proteins: ZO1 (zonula occludens), claudin 5, CD99 and VE-cadherin (vascular endothelial cadherin), and the recovery of the correct apical-basal polarity, they complete the process of morphogenesis of the neo-formed vessels. The combination of such events translates into the generation of new blood vessels. Angiogenesis, however, requires the hierarchical and coordinated organisation of the endothelial cells in TCs and SCs and strict space-time control of gene expression. Studies performed on mice and zebrafish have demonstrated that the VEFG and Notch pathways are fundamental for the specification of the tip and stalk cells during angiogenesis processes in physiological and pathological conditions and that high levels of expression of the exogenous pro-angiogenic factors such as VEGFA and VEGFC (autocrine vascular endothelial growth factors) and of the receptors of VEGF-R2 (VEGFR2, Flk1) and/or VEGF-R3 (VEGFR3, FLT4) induce tip cells to acquire germination and invasion behaviour (Gerhardt et al. 2003; Noguera-Troise et al. 2006; Ridgway et al. 2006; Hellstrom et al. 2007b; Leslie et al. 2007; Lobov et al. 2007; Siekmann and Lawson 2007; Suchting et al. 2007; Phng and Gerhardt 2009; Phng et al. 2009).

Figure 3:
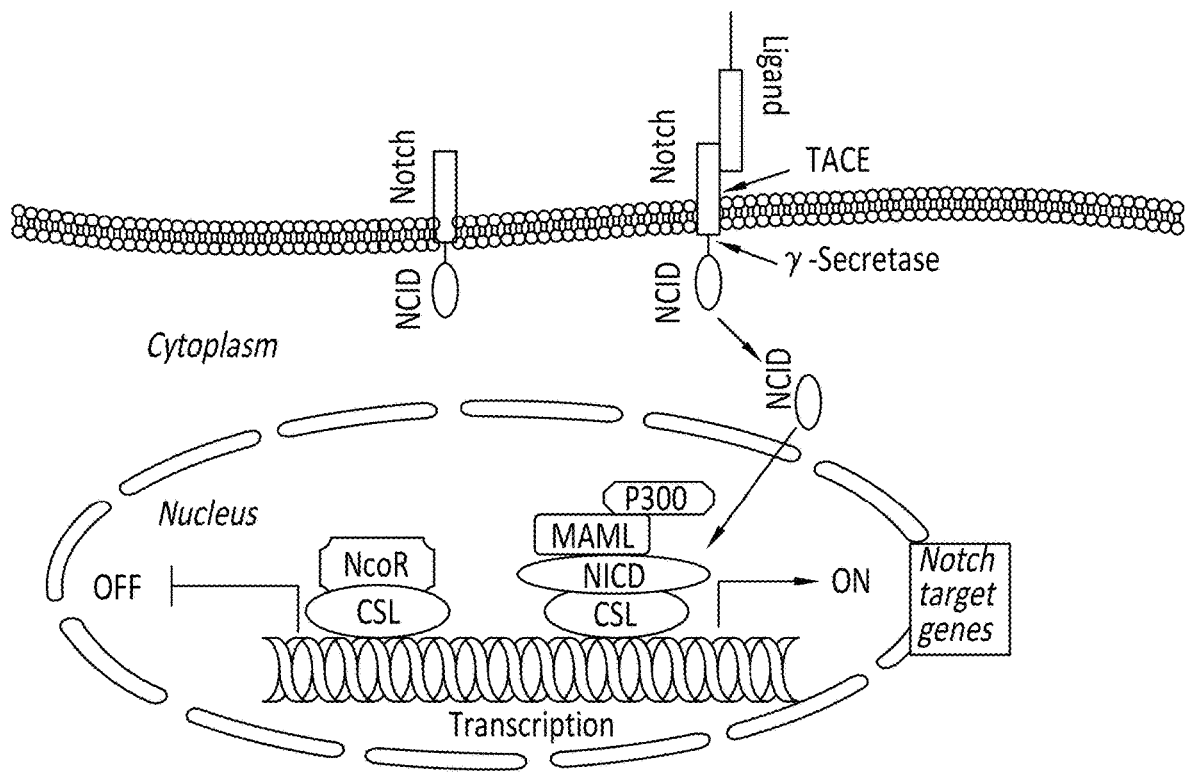

In the cells adjacent to the tip cells, high levels of expression of DLL4 (Delta-Like 4-Notch) were instead found, this protein inhibiting laterally the progression of the tip cell and promoting the stability of the structures of the vessels (FIG. 3). Good coordination of all of said factors that regulate the signalling of Notch is essential to form new vessels and keep pre-existing cells functional. It has been demonstrated that the constituent activation of the Notch pathway induces the formation of defective vessels or even a rupturing of existing vessels (Noguera-Troise et al. 2006; Ridgway J. et al. Nature 2006).

The process of sprouting of endothelial cells in embryonic tissue or in adult tissue, in cases of chronic disease or in acute vascular lesions, is therefore regulated by various factors that inhibit or promote the signalling pathways of Notch/VEGF and is a process comparable to epithelial mesenchymal transition (EMT). EMT, which is a process by means of which the epithelial cells acquire migratory and invasive characteristics, is considered to be a fundamental event during embryogenesis, for the morphogenesis and generation of organs and tissues in vertebrates and invertebrates. A similar process occurs during tumoral invasion and the formation of metastases.

Current research is heavily oriented towards the identification of genes that can modulate the behaviour of the tip cell and of the stalk cell so as to be able to influence sprouting for therapeutic purposes.

Angiogenesis is a paradigm for other types of morphogenetic processes, such as the process that leads to the formation of the lumen in tissues characterised by the presence of cells that are differentiated into tubular structures and undergo branching morphogenesis, such as glandular luminal cells, such as the process of migration of tumoral cells to organs and tissue far from the site of origin or such as processes that regulate the transduction apparatus and the orientation of the axons of the neural cells (Adams R H, Eichmann A. 2010; Herber S P, Stainier D Y R. 2011). Many signalling factors that control angiogenesis in fact also control the formation of the lumen of the ductal and alveolar epithelial structures and the migration of the neural cells (Adams R H, Eichmann A. 2010; Herber S P, Stainier D Y R. 2011). In addition, the migratory and invasive behaviour and the initial phases associated with the formation of the metastases use the same genes and pathways that have been proven to be involved in the formation of blood vessels.

In the case of tumours, for example, it is known that the growth and development of solid tumours is heavily dependent on the formation of new vessels that surround the tumour mass.

Abnormal growth of new blood vessels is also observed in other diseases, such as rheumatoid arthritis, diabetic retinopathy, and psoriasis.

In other pathological conditions, such as in ischaemic cardiac or cerebral pathologies or in the case of damage involving the circulatory system, the induction of angiogenesis instead has a therapeutic effect.

Angiogenesis consists of the development of new blood vessels from pre-existing ones, contrary to primary vasculogenesis, which occurs during embryonic development, in which the endothelial cells form from stem cells. Similarly to that which occurs during the growth of the axons, the tip cells are able to respond to attracting and repelling signals with the aim of defining the trajectory in which the new sprout should be oriented (Gerhardt et al. 2003) and are able to form new connections between different sprouts so as to generate new functional vascular circuits (Isogai et al. 2003).

Angiogenesis is a process of fundamental importance in many physiological processes, such as normal tissue growth, embryonic development, scarring, the menstrual cycle (ovulation), and placenta formation.

On the other hand, angiogenesis is also a fundamental process in many pathological processes. The diseases associated with the angiogenic process can be caused by a low angiogenic activity, such as damage to the tissues following ischaemia or cardiac insufficiency or by an high angiogenic activity, such as chronic inflammation such as rheumatoid arthritis, Crohn's disease, diabetic retinopathy, psoriasis, endometriosis, and cancer.

The development of a blood vessel is in fact an essential phase in the growth and in the development of a tumour. The tumour cells produce (or induce the cells nearby to produce) growth factors that stimulate the formation of blood vessels. In 1971, Folkman hypothesised that the prevention of angiogenesis, depriving the cells of vital nutrients, would be able to inhibit tumour growth.

Angiogenesis is also an essential component in the formation of metastases. New neo-formed blood vessels associated with the tumour mass allow the tumour cells to leave the site of origin and to reach distant organs by means of the bloodstream. The higher is the density of new blood vessels within the tumours, the higher is the risk of metastases.

Since angiogenesis is a fundamental process for the growth of a tumour, many of the anti-tumour drugs studied at that time have the potential to inhibit angiogenesis and therefore limit tumour growth. Thrombospondin for example was the first inhibitor to be discovered in 1989. Another two inhibitors, angiostatin and endostatin, were then identified between 1994 and 1997.

The angiogenic process is characterised by modifications of the endothelium and of the extracellular matrix that can be summarised as follows:
1. Destabilisation of the pre-existing vessels following a rise in the vascular permeability and a loss of the connections between the endothelial cells.
2. Proliferation and migration of the endothelial cells in a zone of the tissue where the formation of new vessels is necessary.
3. Increase of the permeability of the blood vessels; production of proteolytic enzymes that degrade the cellular matrix and facilitate the migration of the endothelial cells.
4. Differentiation of the endothelial cells characterised by a stopping of the cell proliferation and of the formation of primitive capillaries.

It has been demonstrated that Notch/VEGF signalling is of fundamental importance in angiogenesis for the realisation of sprouting, that is to say germination of the capillaries. In the sprouting process, Notch promotes the formation of leading "tip" endothelial cells and determines the distinction between "tip" and the growing "stalk" cells, which will form the capillary. The Notch/VEGF signalling pathway is an evolutionarily conserved mechanism that plays a crucial role in the control of the differentiation of the cells and in cell-fate determination during embryonic development. Current research suggests that Notch/VEGF signalling is not only active during development, but is also fundamental for maintaining adult stem cells, whilst its malfunctioning is associated with the pathogenesis of various human diseases, such as cancer. The Notch/VEGF pathway in fact controls the proliferation and survival of tumour cells, such as tumour progression, and is in fact often activated aberrantly in many metastatic tumours.

In mammals, four genes homologous to the Notch gene identified initially in drosophila have been identified. The 4 Notch genes (Notch 1-4) code for receptors that recognise the ligands Delta-like1, 3, and 4 and Jagged 1 and 2 (Bray, 2006). Such receptors are particularly expressed in cells equipped with stem potential, determine the differentiation thereof, and have a role in a series of processes such as the function and the development of neurons, the formation of the somitomeres, angiogenesis, expansion of the hematopoietic stem cells, and bone development. The Notch receptors are also expressed constitutively in some tumours and are involved in various pathogenetic mechanisms, such as multiple sclerosis, acute lymphoblastic leukaemia, Alagille syndrome, and Fallot tetralogy.

The path of Notch signalling is formed by the transmembrane Notch receptor and by its Delta and/or Jagged ligands. When barely synthesised, the Notch receptors are cleaved by a protease of the Golgi apparatus and transported to the cell surface. This cleavage generates a receptor that is composed of an extracellular region ($N^{EC}$) and a cytoplasmic region ($N^{TM}$). The path of the Notch signal starts with the ligand-receptor interaction between adjacent cells. The interaction between receptors and ligand of the same cell (cis interaction) leads the cell to not generate a signal, due to the degradation of both proteins. The interaction between the receptor of a cell with the ligand of a cell in the vicinity (trans interaction) leads to the release of the Notch intracellular domain ($N^{iCD}$) in the cytoplasm. The $N^{iCD}$ therefore enters the nucleus, where it combines with the transcription factor CSL with consequent successive activation of target genes. Recent studies in fact have revealed the existence of a large number of genes that can be directly regulated by Notch (Krejci et al., 2009; Weng et al., 2006). During the development of vertebrates and in tumorigenesis processes, the inhibition or induction of the differentiation and the start of the proliferation processes represent the most important functions of Notch signalling.

Thus, there is an ever-growing interest in blocking or activating the Notch signal in different contexts and in general, since the process of the formation of a blood vessel, or destruction thereof, are at the root of the onset of many diseases that affect humans, and succeeding in controlling such a process is very important for the therapy of many diseases, besides tumours.

Given the importance of the regulation of angiogenesis in the treatment of many pathologies, there is a need to identify new biological targets that allow angiogenesis regulation for therapeutic purposes.

The genome sequence and the mRNA sequence of the murine and human protein TMEM230 (also transmembrane protein 230) is known in the literature. TMEM230 is a transmembrane protein with no homology with other known genes or proteins of unknown function. In a very recent study, it was demonstrated that the protein TMEM230 was mutated in patients affected by Parkinson's disease and that the protein TMEM230 co-localises with the protein syntaxin 6 in the trans Golgi network (TGN) and in the pre-synaptic vesicles, with RAB5A in the endosomes, and with MAP1LC3A in the autophagosomes of mouse neurons (Deng H X et al. Nat. Genet. 2016).

SUMMARY OF THE INVENTION

The authors of the present invention have found that the protein TMEM230 (described more accurately in the glossary) in embryonic and adult cells plays a role in the regulation of the germination (sprouting) of the endothelial cells, in the epithelial-mesenchymal transition of the epithelial cells, in the invasion and in the migration of epithelial tumour cells, and in anoikis-dependent cell death. Whereas it has been reported that the human gene TMEM230, when mutated, is associated with the aetiology of Parkinson's disease (Deng H X et al. Nat. Genet. 2016) its role in the endothelial cells and in the epithelial cells has not yet been described. The inventors of the present invention have demonstrated that the gene TMEM230 codes for a membrane protein that localises in the secretory vesicles and contributes to the maintenance and regulation of structures containing lumen, such as the vascular and tubuloalveolar epithelial structures. The results were initially generated using the in vivo model system of zebrafish, and then using human endothelial cells obtained from patients, breast and kidney tumour tissues, and normal and tumoral human luminal cell lines. The authors have demonstrated that, depending on the levels of expression, TMEM230 regulates and is necessary for the growth and stability of the vessels, and the fact that the levels of TMEM230 can be modulated makes TMEM230 an excellent biological target for therapeutic purposes.

Whereas the genomic sequence and the mRNA sequence of human and murine TMEM230 are listed in databases, and mutations in the gene sequence have been identified in patients affected by Parkinson's disease (Deng H X et al. Nat. Genet. 2016), the role of TMEM230 in epithelial and endothelial cells has never been described. The endothelial cells form the wall of the blood vessels, whereas the epithelial cells form the wall of the tubules, of the ducts and of the alveoli of many organs and tissues. The endothelial cells and the epithelial cells separate the blood and bodily fluids from other tissue components and form a barrier of selective permeability, achieved by means of the coordinated opening and closing of the cell-cell junctions. Such junctions have a critical role in the transduction of the mechanical and chemical signals that regulate the inhibition of contact growth, apoptosis, gene expression, and the formation and stability of vessels.

The endothelial cells rarely divide (once every 3 years), however, when the situation requires, the activation of the process of angiogenesis can induce said cells to divide.

The authors have demonstrated for the first time that TMEM230 is a regulator of the Notch/VEGF signalling path and can compensate, correct and modulate the Notch/VEGF pathway. However, the modulation of TMEM230 can be used for therapeutic purposes in all of those cells and in those conditions in which regulation of the Notch/VEGF pathway is necessary, both within the scope of regenerative medicine and within the scope of antitumour therapy.

In particular, the authors have found that the gene TMEM230 is a regulator of the Notch signalling path in various types of cells, for example endothelial cells and epithelial cells and glandular cells that form luminal structures associated with the formation of tubular/ductal and alveolar structures. The authors have demonstrated that TMEM230 also plays an independent role in the Notch pathway and is involved in the regulation of the processes involved in cellular migration, invasion and sprouting of epithelial and endothelial cells and regulates anoikis-dependent cell death.

The authors have also demonstrated that the modulation of the level of expression of TMEM230 can be used to promote the dormant state or to induce cell sprouting, migration and invasion and that therefore the modulation of the activity of TMEM230 (at gene expression, transcription or protein level) can be used not only to inhibit or induce angiogenesis, but also to promote or prevent the acquisition of invasive and migratory behaviour by the cells.

The data obtained by the authors of the present invention has thus proven that in the case of diseases in which an increase of angiogenesis is desired, alternative cycles of transient overregulation of the expression of TMEM230 followed by a reduction thereof produce the desired effect.

Since the data produced by the authors demonstrates that TMEM230 regulates sprouting, invasion, and migration within the scope of the Notch/VEGF pathway, but that TMEM230 also has a role in the regulation of cell sprouting and invasion independently of Notch/VEGF and that specific levels of TMEM230 are necessary and sufficient to control the sprouting dormancy and behaviour, the authors suggest that the level of TMEM230 expression and the management of its modulation should be determined by an expert clinician in the field for each patient for whom therapeutic angiogenesis regulation is deemed necessary.

In the present patent application, reference to "high" or "low" levels of expression refer to the levels encountered in a healthy counterpart of the same organ, tissue or cell. In this specific case, reference is made by way of example to the levels of TMEM230 of vessels in non-pathological conditions, or in epithelial cells of normal tissues. The overregulation or underregulation of such TMEM230 expression levels compared to the levels of expression encountered in healthy cells are responsible for the establishment of pathological conditions that translate into diseases associated with defects in the angiogenic processes, which in turn can be attributed to low angiogenic activity, for example tissue damage following ischaemia or cardiac insufficiency, and pathological conditions caused by high angiogenic activity, such as chronic inflammation, rheumatoid arthritis, Crohn's disease, diabetic retinopathy, macular degeneration associated with age, psoriasis, endometriosis, and cancer.

In the present description, when it is stated that the expression of TMEM230 is overregulated or underregulated or also increased or reduced, this means that the expression of the gene or of the protein TMEM230 is regulated positively or negatively compared to the level of expression present in the treated patient at that moment, and therefore a positive regulation will lead to an increase of the expression or activity of TMEM230 in the treated tissues of the patient, whereas a negative regulation will lead to a reduction of the expression or activity of TMEM230 in the treated tissues of the patient. The regulation can be performed at nucleic acid level or at protein level.

Pathologies in which the Formation of New Blood Vessels is Required.

For the formation of new blood vessels, the authors have demonstrated (as detailed in the examples section) that, in human endothelial cells derived from patients, alternate cycles in which high levels of expression of the gene, of the mRNA, or of the protein TMEM230 followed by cycles in which said levels of expression are kept low induce the formation of new blood vessels. The overregulation of the levels of expression of the gene, the mRNA or the protein TMEM230 in the endothelial cells of the existing blood vessels translates into the destabilisation thereof as a result of the increase of the "local" permeability caused by the loss of cell-cell contacts. All of this occurs only in a small minority of cells, which are those selected to become tip cells. The loss of cell-cell contacts is followed by the sprouting of the tip cells. The sprouting of the tip cells is followed by the proliferation thereof, however, in order for the formation of the new vessel to be completed, said cells have to be reconverted into non-tip, non-proliferating cells, and the cell-cell contacts must be recreated in order to prevent the destruction of the existing vessels. The levels of expression of TMEM230 must therefore be re-established or the agent used to induce the overregulation of TMEM230 must be removed or an agent must be used that allows transient underregulation so as to allow the reduction of the expression of the gene, the mRNA or the protein TMEM230 and allow the formation of stalk cells and the re-establishment of intercellular contacts, which close the walls of the new vessels and ensure the stabilisation thereof, thus leading to the definition of the new lumen.

Thus, alternating between high and low levels of expression of TMEM230 as described above and in the present description has the therapeutic effect of promoting angiogenesis in diseases or pathological conditions in which the formation of new blood cells and an increase in angiogenesis are desired.

Diseases in which a Reduction of Angiogenesis is Required.

In diseases, instead, in which high angiogenic activity is encountered and in which a reduction of angiogenesis is desired, a reduction of the expression of TMEM230 can produce such an effect. Since high levels of TMEM230 induce sprouting, whereas a reduction of the expression levels of TMEM230 promotes the state of dormancy and maintenance of cell-cell contacts, which is vital for maintaining and stabilising the 3D structures containing lumen (vessels, tubules, ducts, alveoli and acini) and since TMEM230 can also have an independent role from the Notch/VEGF pathway, the authors suggest that the level of expression of TMEM230 and the direction in which TMEM230 should be modulated must be determined on a patient-by-patient basis.

Tumoral Angiogenesis

Figure 4A:
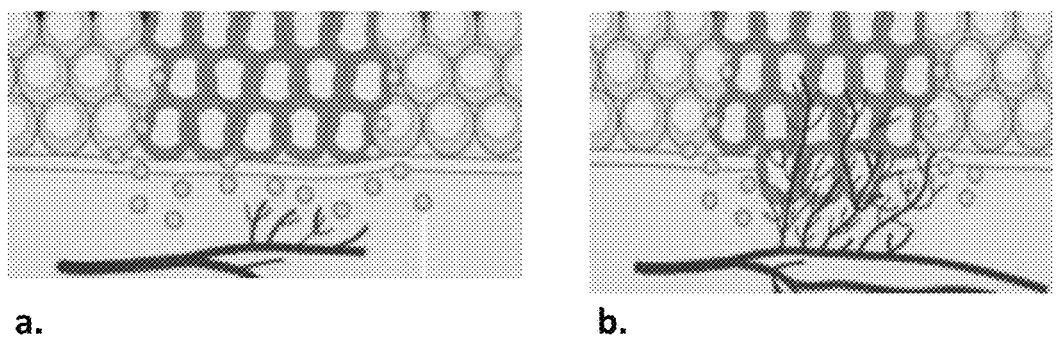

In tumoral diseases, for a tumour to develop it is necessary for the blood vessels to form an extended network of new branchings that integrate within the tumour mass for the purpose of providing the tumour with nutrient substances and oxygen (FIG. 4A). In tumours, the modulation of TMEM230 can be performed for many purposes: 1. To inhibit tumoral angiogenesis. 2. To destroy the blood vessels already permeating the tumour. 3. To prevent the tumour from growing, thanks to the ability of TMEM230 to inhibit cell migration and thus block the access of the tumour cells to the circulatory system, through which they start to circulate as circulating cancer cells so as to reach organs and tissues far from the primary tumour. 4. To inhibit the invasion and metastatisation associated with the migration of the tumour cells.

The authors have surprisingly found that, in fact, in the early stages of tumour formation, when the tumour has not yet developed its own network of capillaries sustaining its growth and expansion, a transient reduction of the expression or activity of TMEM230 (at DNA, mRNA or protein level) has the effect of both inhibiting neoangiogenesis, since it prevents the generation and branching of new vessels towards the tumour mass (FIG. 4B), and of blocking the migration of the luminal tumour cells, thus preventing them from invading and reaching the bloodstream. In addition, the transient under-expression of TMEM230 has the effect of making the tumour cells incapable of living in anchorage-independent conditions (in that in order to circulate in the bodily liquids they need to grow in suspension), therefore facilitating the cellular death thereof by anoikis. Thus, the underregulation of TMEM230 has the objective of inhibiting the germination of new vessels in the direction of the tumour and of hindering the ability of the tumour cells to live in anchorage-independent conditions, thus making them incapable of circulating in suspension in the circulatory system, which is, moreover destabilised.

By contrast, in more advanced stages of the tumour (FIG. 4B), a localised increase of the levels of expression of TMEM230 leads to the destabilisation/destruction/disaggregation of the existing blood vessels. In this case, angiogenesis is inhibited by means of destruction of the vessels, caused by a loss of the integrity thereof, achieved by increasing the expression, at DNA or mRNA or protein level, and consequently the levels, of TMEM230.

A transient overexpression (protracted until the desired effect is obtained) of the expression or activity of TMEM230 in the endothelial cells of the vessels that supply the tumour provokes a rupturing of the blood vessels with the subsequent arrest of tumour growth due to destruction of the tumour cells.

The overregulation of the levels of expression or activity of TMEM230 in tumours already provided with an efficient network of blood vessels can therefore have a number of advantages, such as: 1. it can lead to the destruction of the existing blood vessels that provide nutrients and oxygen to the tumour; 2. it can prevent the formation of metastases insofar as, because the tumour cells are unable to circulate within the blood vessels destroyed in this way, they cannot diffuse into other organs and tissues.

Thus, on the basis of that disclosed herein for the first time, it would appear that TMEM230 is an ideal target for antitumour therapies in accordance with two modes of action:

1. In early neoplastic lesions, in order to prevent the tumours from becoming larger and the tumour cells from being able to reach organs and tissues distant from the site of origin, and in order to prevent the formation of new blood vessels, it is necessary to prevent sprouting and formation of tip cells. In order to do this, it is fundamental to maintain low levels of TMEM230 in all the endothelial cells of all the blood vessels of the tumour for the duration of the antitumour therapy. Without neoangiogenesis, the tumour cannot grow and the tumour cells cannot invade new tissues (FIG. 4C). Reduced levels of TMEM230 in the tumour epithelial cells, reversing the mesenchymal phenotype to a phenotype more similar to the epithelial phenotype, induce a loss of invasive capability, thus promoting the mesenchymal-epithelial transition (MET). Since the invasive cells are associated with a phenotype more similar to the mesenchymal phenotype, when the cell regains the epithelial-like phenotype it loses its migratory and invasive capabilities and its resistance to anoikis, thus losing its ability to survive in suspension, and is no longer able to circulate in the bodily liquids and cannot reach sites far from the site of origin (FIG. 4C, box a.).

2. In advanced-stage tumours, in which the blood vessels associated with the tumour are instead already formed, it is necessary for the levels of expression of TMEM230 to be kept high in order to induce sprouting and achieve destruction of the cell-cell contacts and destabilisation and rupturing of the blood vessels themselves. Depriving the endothelia of the cell-cell contacts results in the formation of cracks along the vessels with a subsequent loss of their functionality. The levels of expression of TMEM230 in this condition must therefore be kept overregulated as long as necessary in order to prevent the cells of the endothelia from being able to re-establish the cell-cell contacts and thus rebuild the lumen of the vessels.

Although the overregulation of TMEM230 in the luminal cells of the vessels associated with the tumour can lead, in the luminal tumour cells, to an increase in invasive capability, these cells cannot survive insofar as they do not have a supply of nutrient substances in loco and the tumour mass is devoid of functional blood vessels, and therefore they cannot reach organs and tissues far from the site of origin insofar as they cannot access vessels that are in a state of disintegration (FIG. 4C, box b).

In conclusion, in the early stages of the formation of a tumour (initial tumour), a reduction of the expression of TMEM230 is necessary in order to block neoangiogenesis and prevent the formation of tip cells and the branching of new blood cells, and therefore in order to prevent the tumour cells from invading and reaching the bloodstream. In advanced stages of the tumour, an overregulation of the levels of expression of TMEM230 in the endothelial cells that form the vessels associated with the tumour provokes a rupturing of the blood vessels with a subsequent arrest of tumour growth.

The invention therefore relates to agents that modulate/regulate the activity of the protein TMEM230 for use in the treatment of diseases in which angiogenesis regulation is necessary or advisable; a pharmaceutical composition for use in the treatment of diseases in which angiogenesis regulation is necessary or advisable, comprising one or more agents which modulate/regulate the activity of the protein TMEM230 and at least one pharmaceutically acceptable carrier; a pharmaceutical kit for sequential use in the treatment of pathologies in which angiogenesis regulation is necessary, comprising at least one vial containing a regulator of TMEM230 that induces transient overregulation of TMEM230 and at least one vial containing a regulator of TMEM230 that induces a transient underregulation of TMEM230, wherein said pathology is a tumour; a therapeutic treatment that provides the administration of pharmacologically effective doses of one or more agents which modulate/regulate the activity of the protein TMEM230 simultaneously or in succession, in a subject suffering from a pathology in which angiogenesis regulation is necessary or advisable.

DETAILED DESCRIPTION OF THE FIGURES

FIG. 1. Schematic view of the angiogenesis process. FIG. 1A. Formation of new blood vessels from existing vessels. FIG. 1B. Angiogenesis is necessary in tissue repair and regeneration processes following injury.

Figure 2:
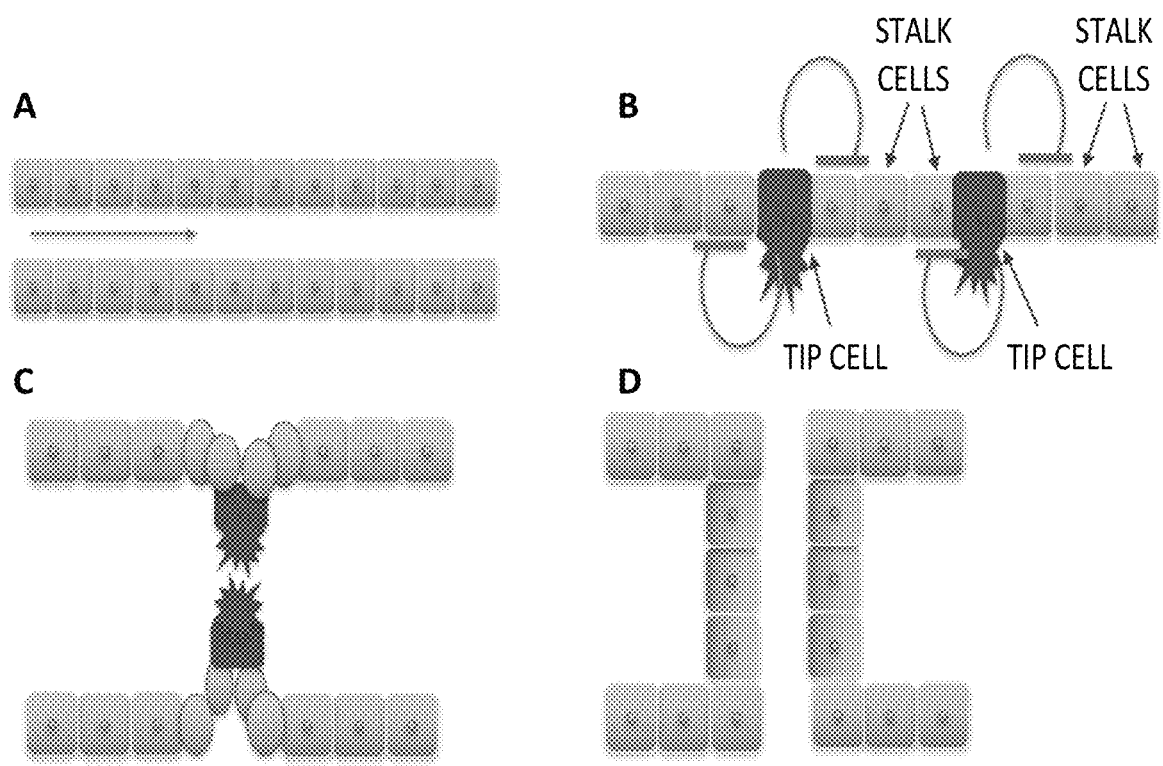

FIG. 2. View of the sprouting process activated by pro-angiogenic factors. FIG. 2A. Vessel formed from dormant endothelial cells. FIG. 2B. During sprouting, the endothelial cells adopt the tip phenotype and the stalk phenotype. FIG. 2C. Migration and proliferation allow the tip cells to connect and form the new lumen. FIG. 2D. The neoformed vessel then matures and stabilises.

FIG. 3. Illustrative schema of the Notch pathway.

FIG. 4A. Example of tumour angiogenesis. a. In the initial phases of the tumour the tumour cells grow in the absence of their own vascular network. b. As the tumour mass develops in conditions of hypoxia, pro-angiogenic factors are released by the tumour for the purpose of inducing the germination of new vessels.

Figure 4B:
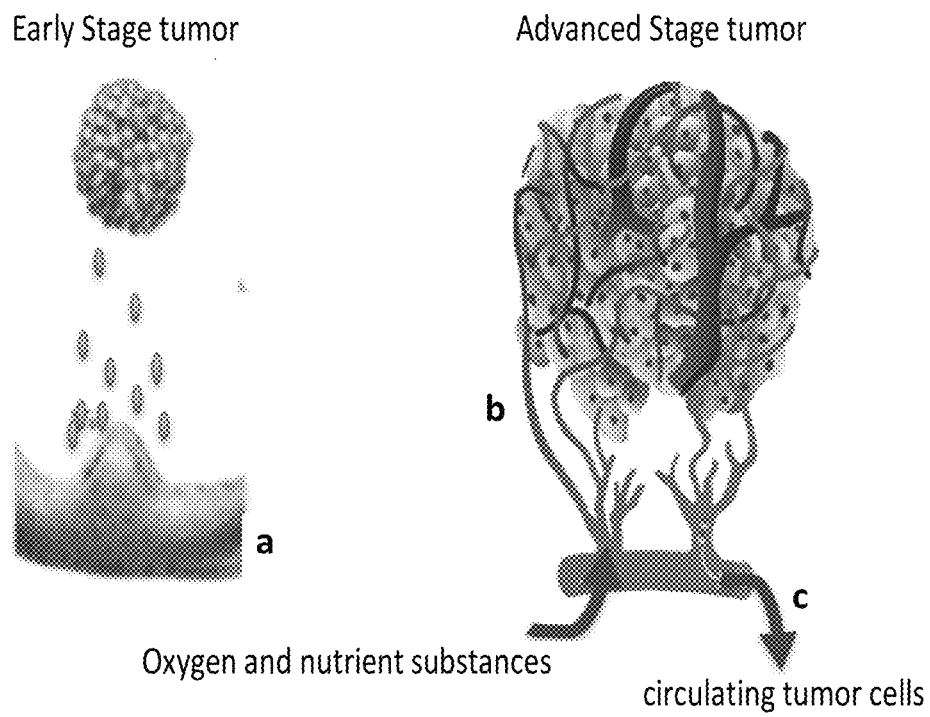
Figure 4C:
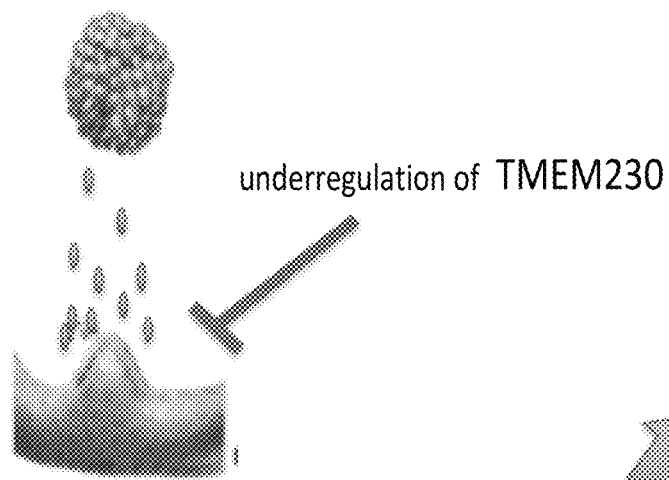
Figure 4C:
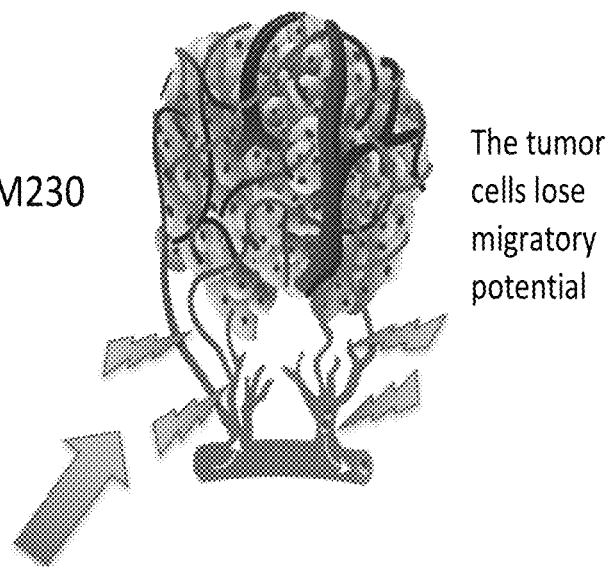

FIG. 4B. The new branchings migrate in the direction of the tumour mass (a) and become integrated therewith (b) for the purpose of supplying the tumour with nutrient substances and oxygen and facilitating the growth thereof. The network of new vessels also allows all tumour cells to move away from the tumour, (c) enter the bloodstream, and reach other organs and tissues where they can take root and give rise to metastatic tumours.

FIG. 4C. The overregulation of TMEM230 induces a reduction of the tumour mass. a. In the early stages of the tumour, the underregulation of TMEM230 opposes sprouting. b. In the advanced stages of the tumour, the overexpression of TMEM230 induces destabilisation of the capillaries that supply the tumour, leading to a subsequent reduction of the tumour mass due to an absence of nutrients. At the same time, the formation of metastases is blocked because the epithelial cells are unable to invade and enter the compromised circulatory system. In both cases the result is a reduction of the tumour mass.

Figure 5:
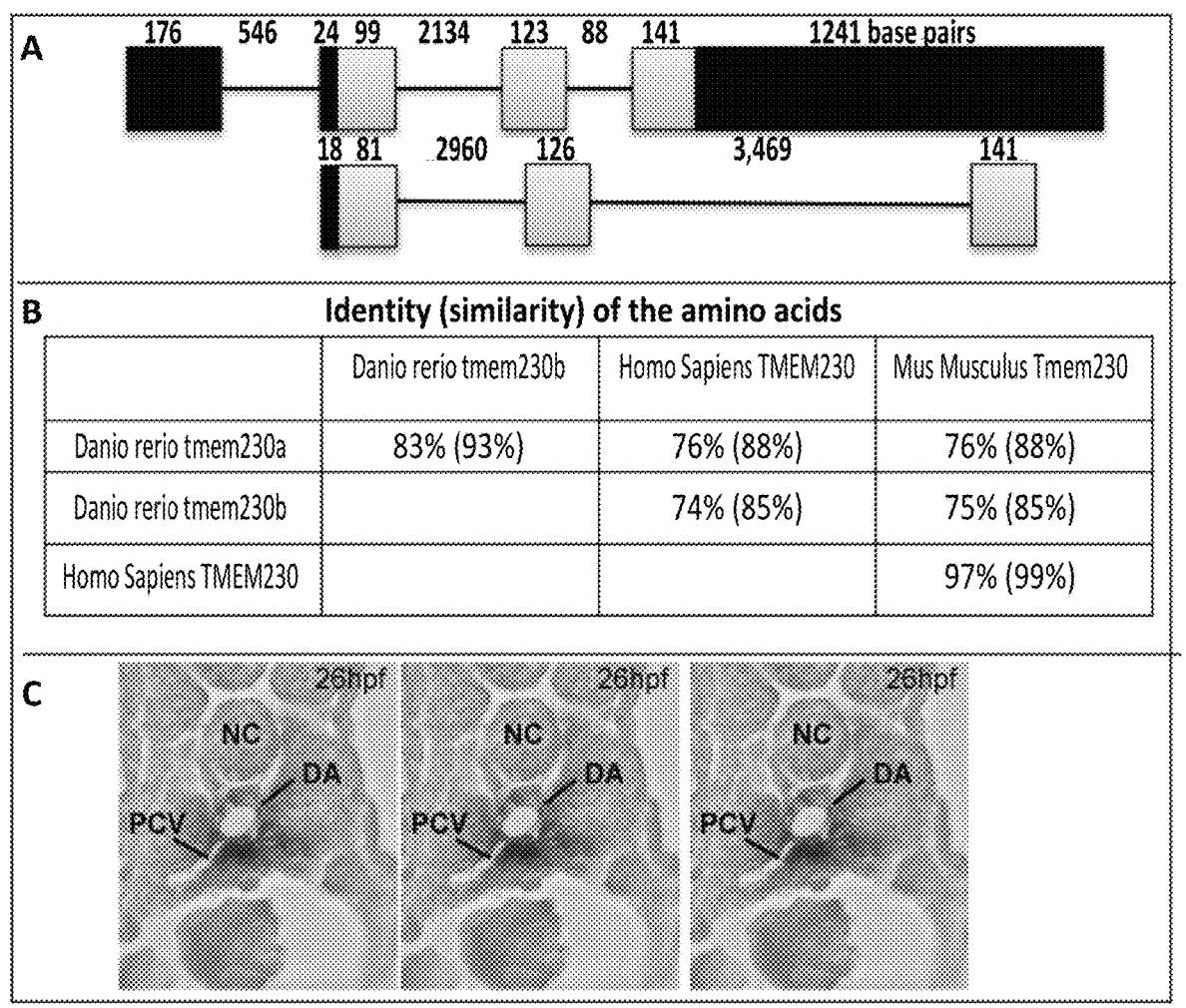
Figure 6A:
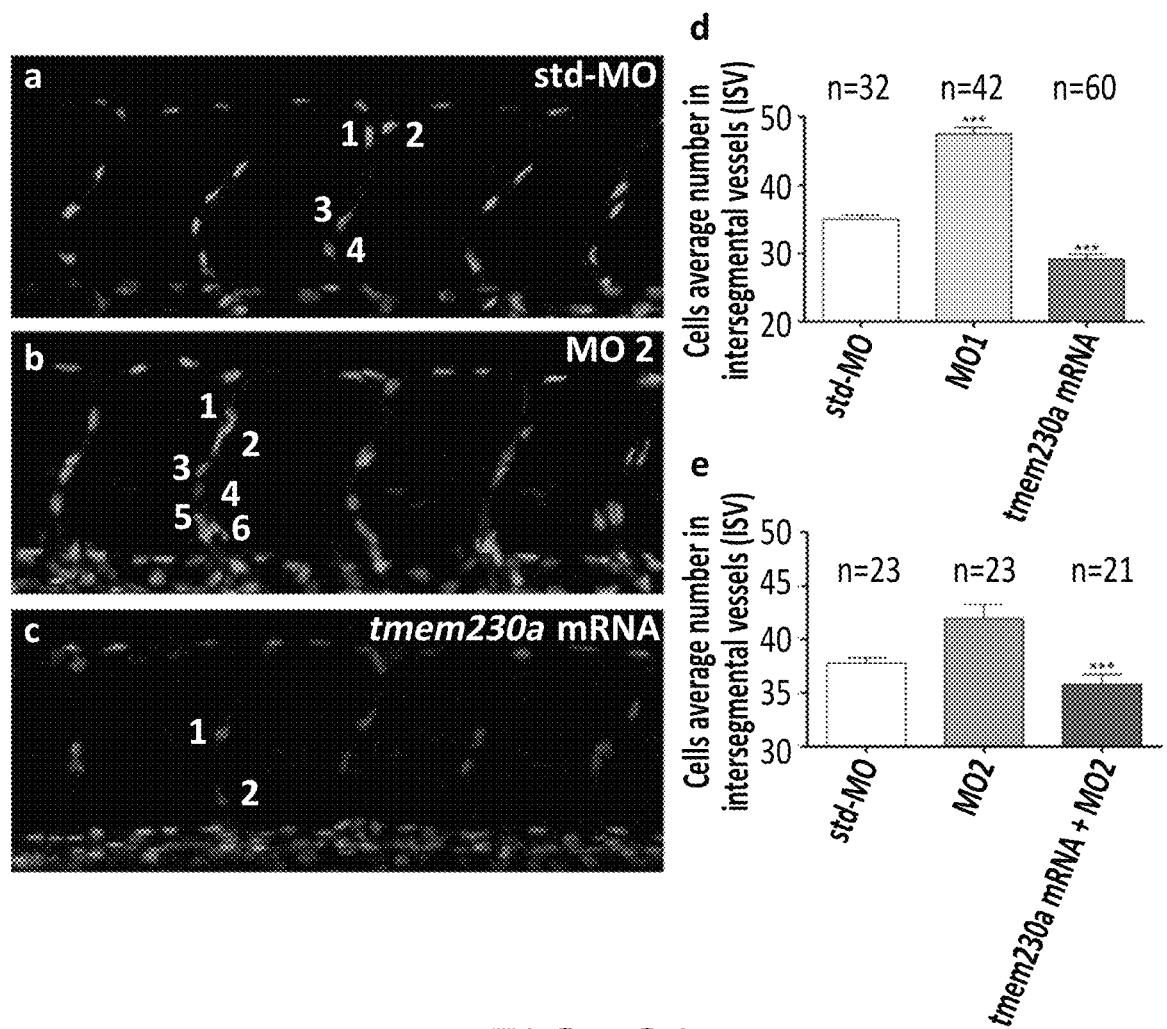
Figure 6B:
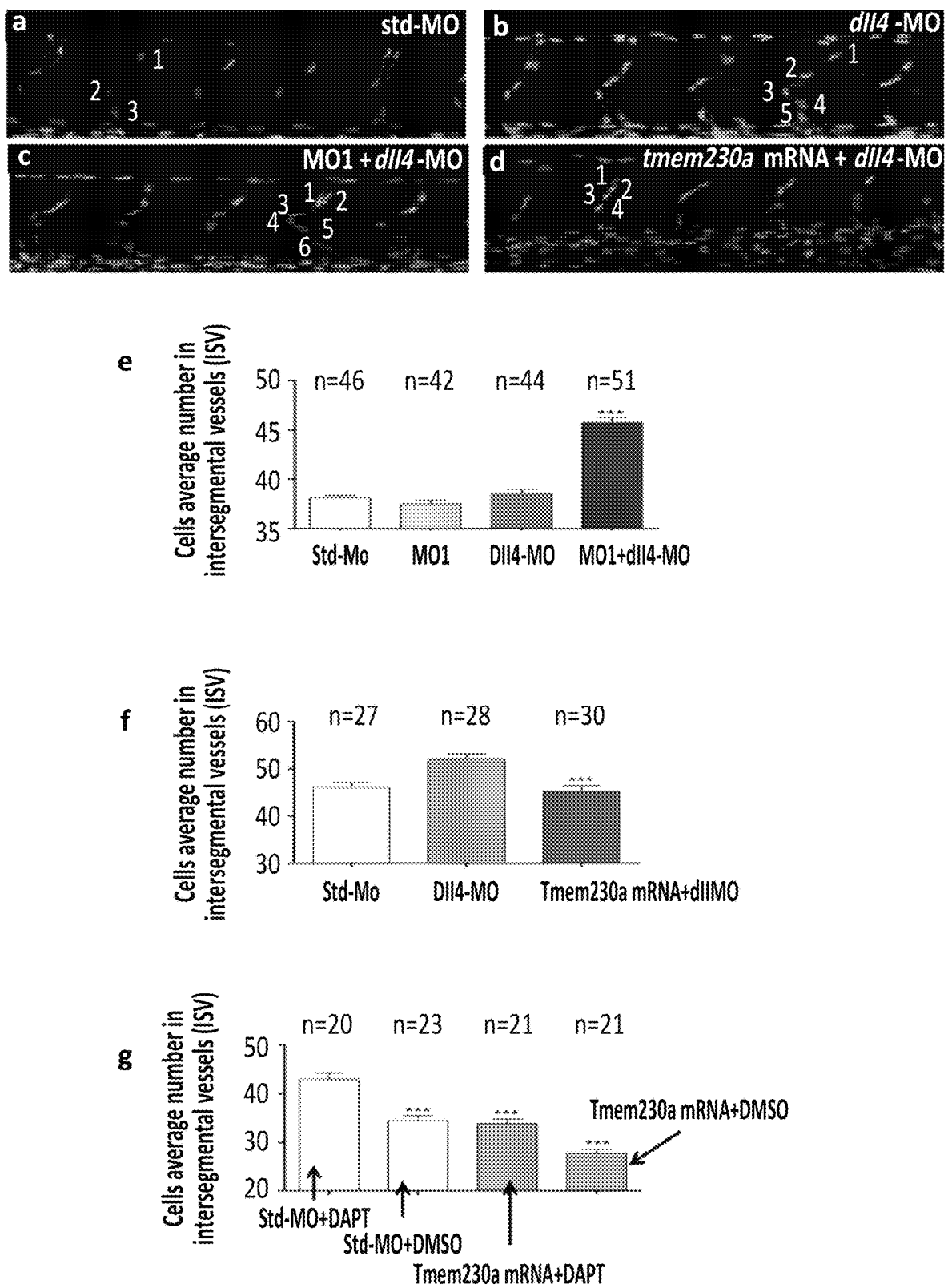
Figure 6C:
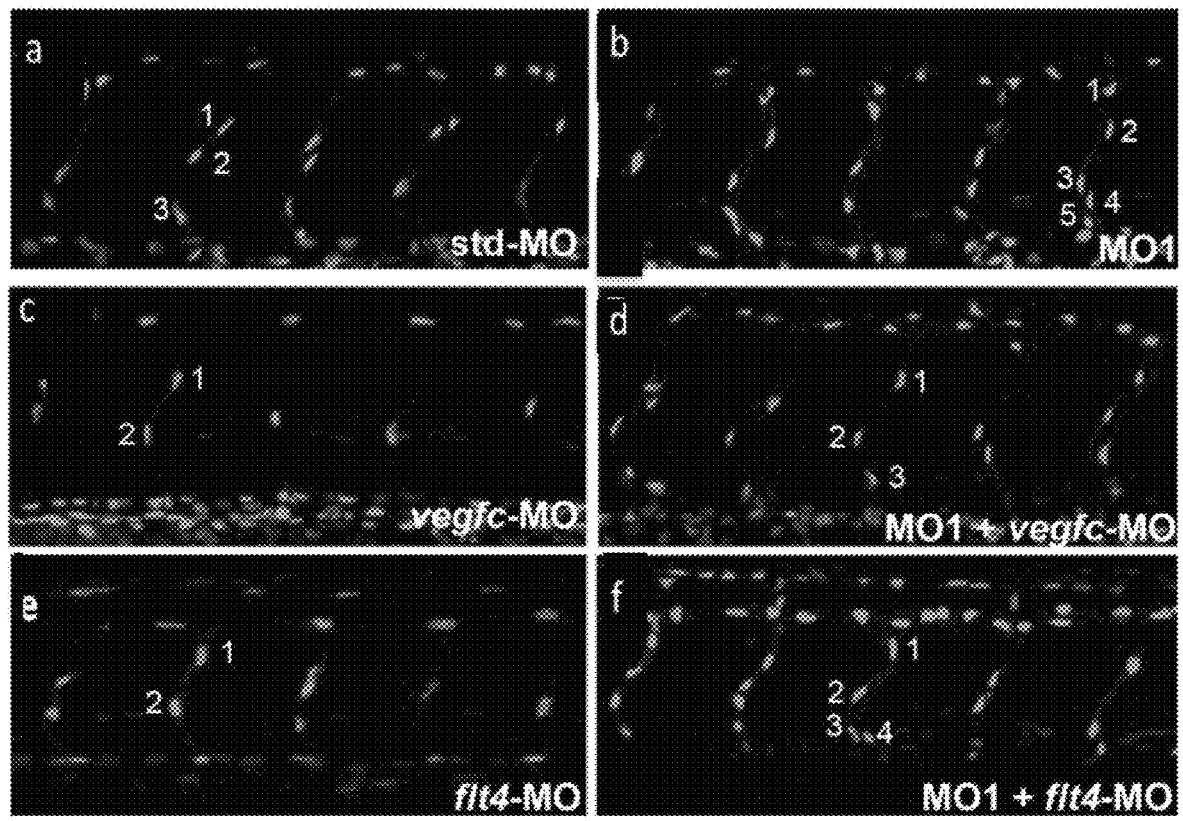
Figure 6C:
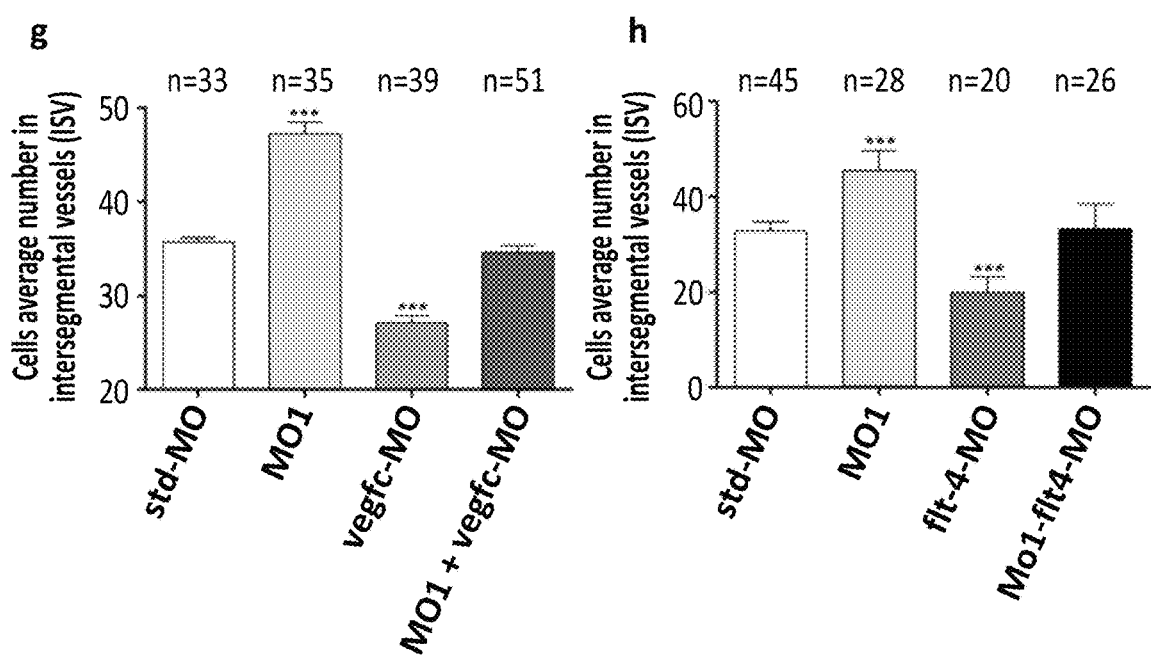
Figure 6D:
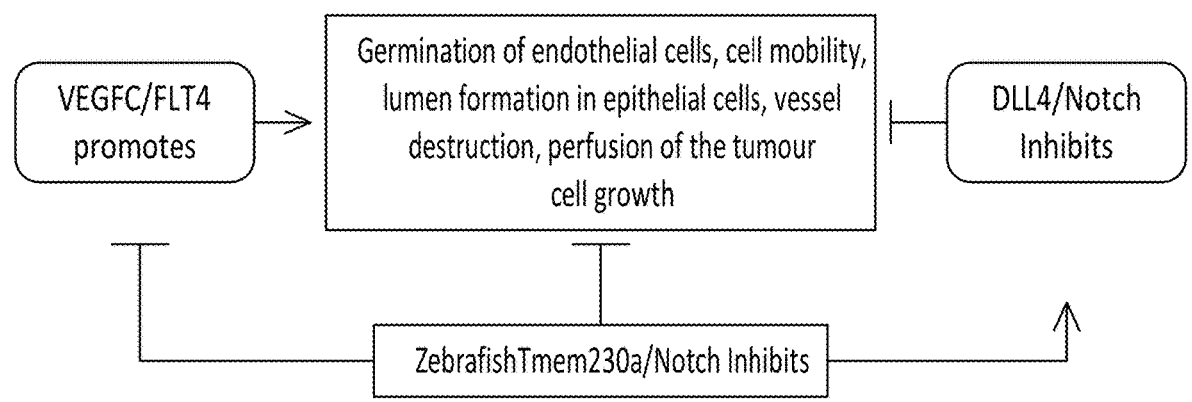

FIG. 5. Structure of the Tmem230 gene of zebrafish, conservation in the species and analysis of expression by hybridisation in situ with a probe complementary to mRNA-Tmem230a. FIG. 5A: View of the structure of the Tmem230a gene and of the paralogous Tmem230b gene in zebrafish. The introns are represented by lines, the exons are represented by rectangles. The untranslated regions are dark rectangles, whereas the coding regions are clear rectangles. FIG. 5B: The comparative analysis of the sequence of the protein shows that the Tmem230 proteins are evolutionally conserved. FIG. 5C: Analysis of the expression of mRNA-Tmem230 obtained by hybridisation in situ in embryos of zebrafish. The sections were hybridised with a probe complementary to the sequence of the mRNA of Tmem- 230a. Embryos at 26 hours after fertilisation (26 hpf) reveal expression of Tmem230a in the midsection (left) and at the tail (middle). Embryos at 2 days after fertilisation (2dpf) reveal expression of Tmem230a at the tail (right). The histological analysis shows the expression of Tmem230a in the dorsal aorta (DA), where there is early angiogenesis, in the posterior cardinal vein (PCV), in the caudal vein (CV) and in the notochord (NC) and shows the role of Tmem230a in vasculogenesis and in angiogenesis.

FIG. 6. Tmem230a regulates the key modulators of the Notch signalling pathway in zebrafish. FIG. 6A: Injections of morpholino oligos against Tmem230a (MO2) produce a rise in the number of endothelial cells (b) compared to that observed after injection of control morpholino oligos (a) (std-MO). The injection of mRNA of Tmem230a restores the correct number of endothelial cells that form the intersegmental vessels (ISV) (c). FIG. 6B: Injections of subcritical doses of morpholino oligos against Tmem230a (MO1) and against dII4 (dII4-MO) synergistically reduce the number of ISV cells (box c) compared to that observed with injections independent of subcritical doses of morpholino MO2 against Tmem230a or of morpholino against dII4 (dII4-MO) (b). The co-injection of mRNA Tmem230a restores the correct number of endothelial cells (d). The embryos were injected with standard morpholino oligos (std-MO) and with sub-critical doses of MO1 (Tmem2301a) or of DII4-MO, and of MO1 and DII4-MO together. FIG. 6C: the phenotype Tmem230a-MO1 (b) is recovered by the injection of morpholino vegfc-MO (d) and by morpholino flt4-MO (f). The embryos were injected with: std-MO (a), Tmem230a-MO1 (b), vegfc-MO (c), Tmem230a-MO1 and vegfc-MO together (d), flt4-MO (e) and Tmem230-MO1 and flt4-MO together (f). The images captured by confocal microscope show the number of endothelial cells in the ISV at 29 hpf in embryos obtained from the line tg (flii: nEGFP)$^{y7}$. The number (n) indicates the injected embryos and is shown in the graph. FIG. 6D: Summary of the role of Tmem230a in zebrafish.

Figure 7:
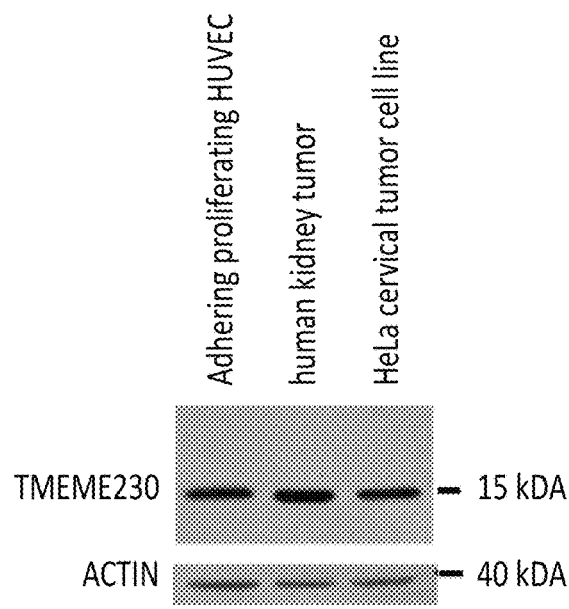
Figure 7:
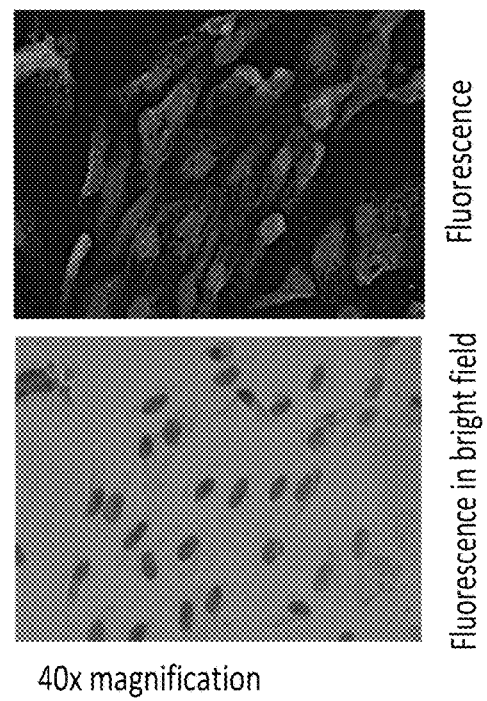

FIG. 7. Analysis of the expression of the human protein TMEM230. (left) Expression of the TMEM230 protein in human umbilical vein endothelial cells (HUVEC), in kidney tumours obtained from patients and in a tumour cell line derived from the cervix (HeLa). (right) Immunohistochemical analysis of the TMEM230 protein in HUVEC cells involved in adhesion.

Figure 8:
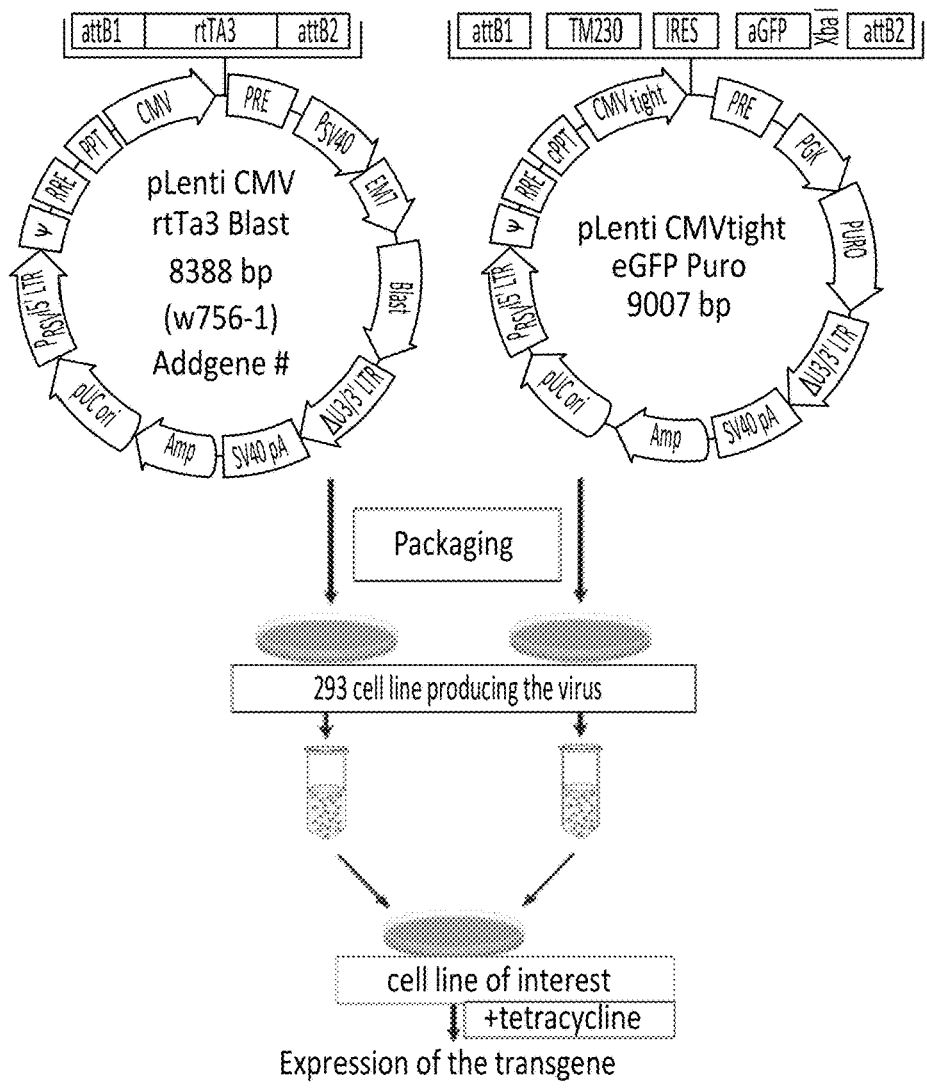
Figure 8:
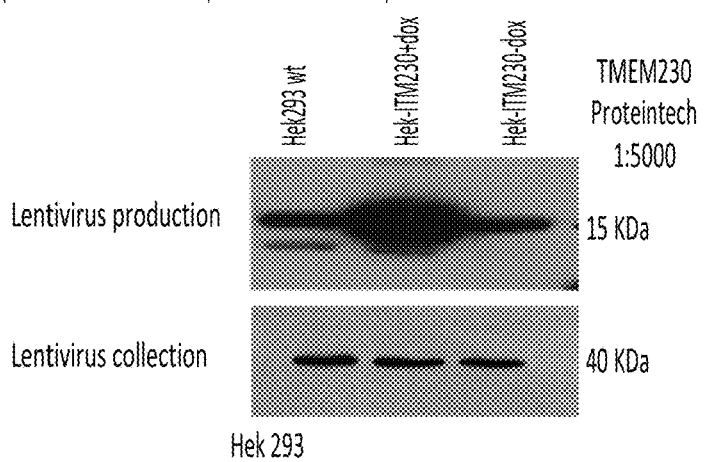

FIG. 8. Inducible lentiviral constructs designed and produced so as to obtain an efficient rise in the levels of TMEM230. The rise in the level of expression of the TMEM230 protein was assessed by means of Western analysis, using HEK cells (human embryonic kidney cells), in which the construct was transduced. Actin was used as gel loading control protein.

Figure 9A:
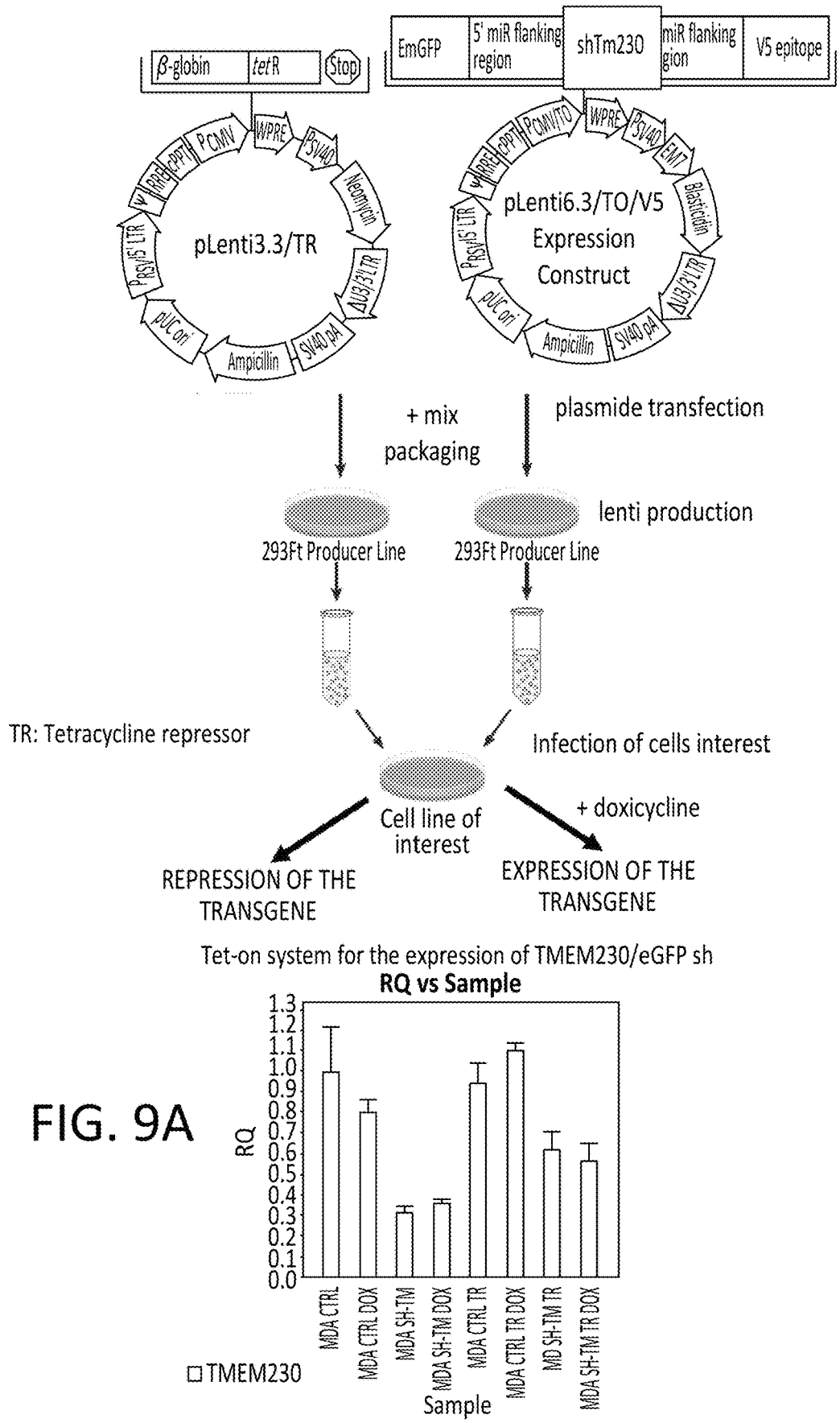

FIG. 9A. Inducible lentiviral cells designed and produced so as to obtain an efficient reduction of the levels of TMEM230.

Figure 9B:
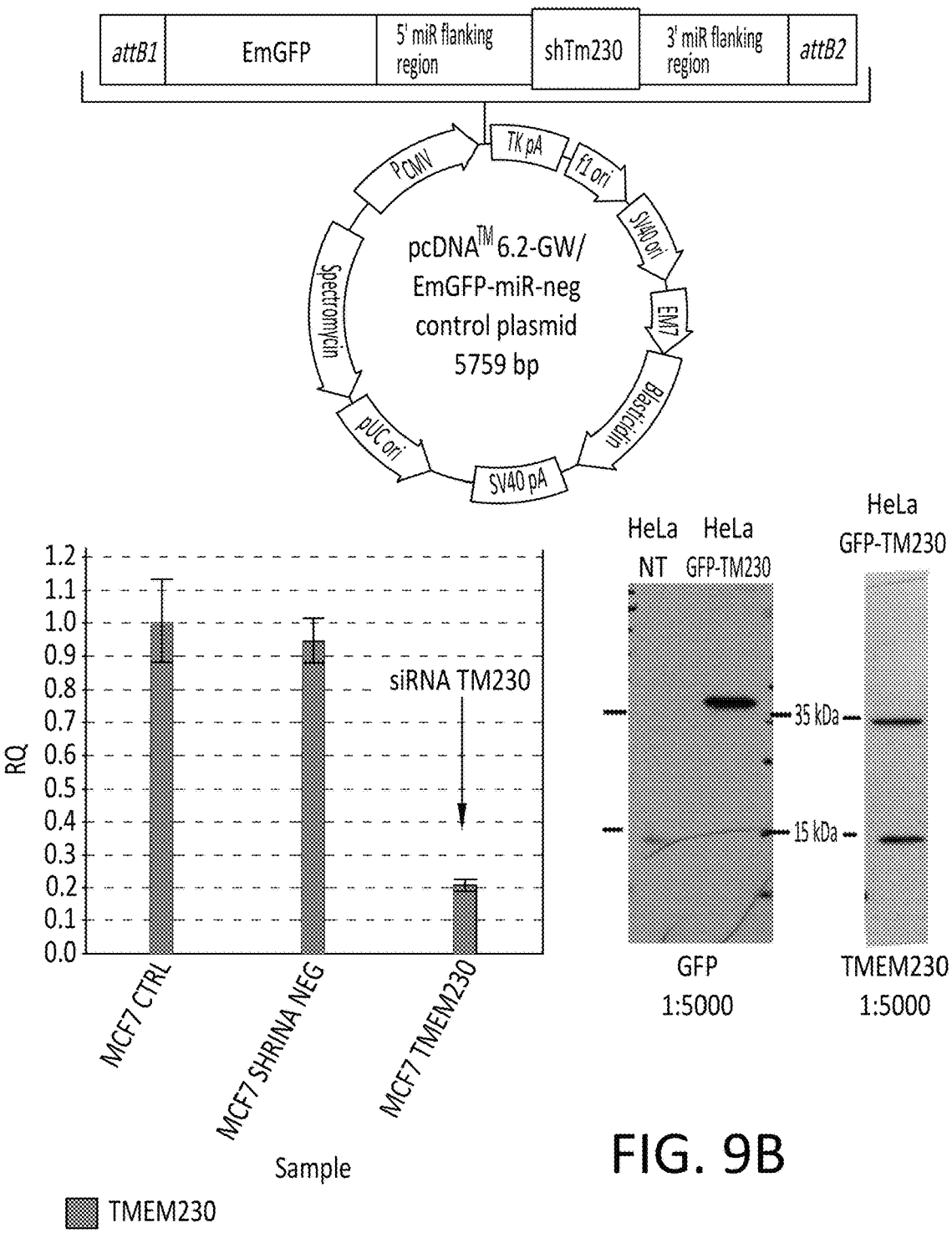

FIG. 9B. Constructs produced in laboratory for the stable underregulation of Tmem230, using siRNA sequences and demonstration by RTPCR of the realised underregulation of the mRNA or TMEM E230 (right).

Constructs for the stable expression of the TMEM230 protein as protein merged with the eGFP protein (left) and Western analysis to verify the expression of the protein in HeLa cells.

Figure 10:
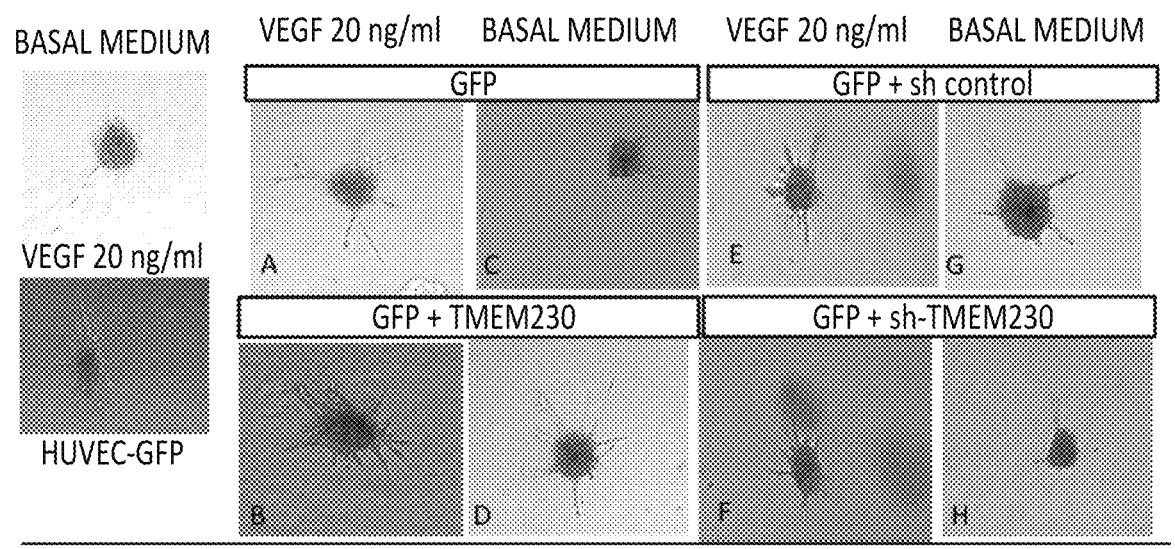

FIG. 10. Modulation of the TMEM230 protein and evaluation of its role in the modulation of sprouting and migration induced by VEGF in HUVEC cells. Images showing spheroids produced by HUVEC cells transduced with lentiviral constructs that express the transgene that expresses only eGFP (eGreen Fluorescent Protein) used as control (FIGS. 10A and 10C), or with the TMEM230 transgene co-expressed with the transgene that expresses eGFP (FIGS. 10B and 10D); with the transgene that expresses control siRNA (sh-GFP, FIGS. 10E and 10G) and siRNA-TMEM230 (FIGS. 10F and 10H) FIG. 10A: Spheroids produced by HUVEC cells in the presence of VEGF. FIG. 10B: The overregulation of TMEM230 in HUVEC cells in the presence of pro-angiogenic factors (VEGF) induces an increase in sprouting and migration compared to the control of FIG. 10A in which TMEM230 was not overregulated (suggesting that TMEM230 and VEGF are synergistic). FIG. 10C: Spheroids produced from HUVEC cells in the absence of VEGF. FIG. 10D: The overregulation of TMEM230 in the absence of VEGF, increases sprouting and migration compared to the condition in which TMEM230 was not overregulated (FIG. 10C), showing that TMEM230 is sufficient alone to promote sprouting in human endothelial cells, similarly to that induced by the pro-angiogenic stimulus. FIG. 10E: Spheroids produced by HUVEC in the presence of VEGF. FIG. 10F: The underregulation of TMEM230 induced by lentiviruses expressing siRNA that breakdown TMEM230, in the presence of VEGF significantly reduced the sprouting associated with angiogenesis, showing that TMEM230 is sufficient to suppress and modulate sprouting and is necessary for VEGF-dependent angiogenic sprouting. FIG. 10G: Spheroid produced from HUVEC cells in the absence of VEGF. FIG. 10H: The underregulation of TMEM230 in the absence of pro-angiogenic factors (VEGF) reduces the basal level of sprouting compared to the control, showing that the reduction in the levels of TMEM230 can repress cell migration and invasion.

Figure 11:
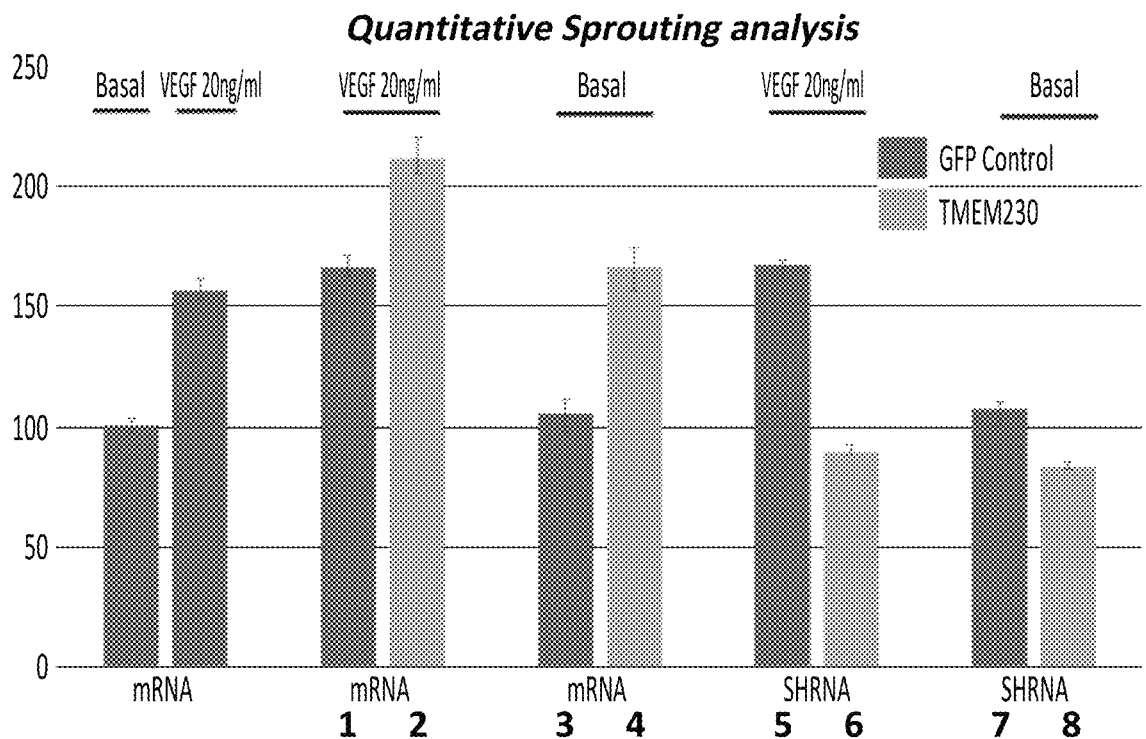

FIG. 11. Quantitative analysis of sprouting for the experiments shown in FIG. 10 obtained by means of microscopic differential bright field density image analysis. The overregulation of TMEM230 has a positive effect on sprouting in basal conditions (cfr. columns 2 & 4) and a synergistic effect with VEGF on sprouting (cfr. columns 1 & 2). The underregulation of TMEM230 significantly reduced sprouting both in basal conditions (cfr. columns 7 & 8) and in the presence of VEGFs (cfr. columns 5 & 6).

Figure 12:
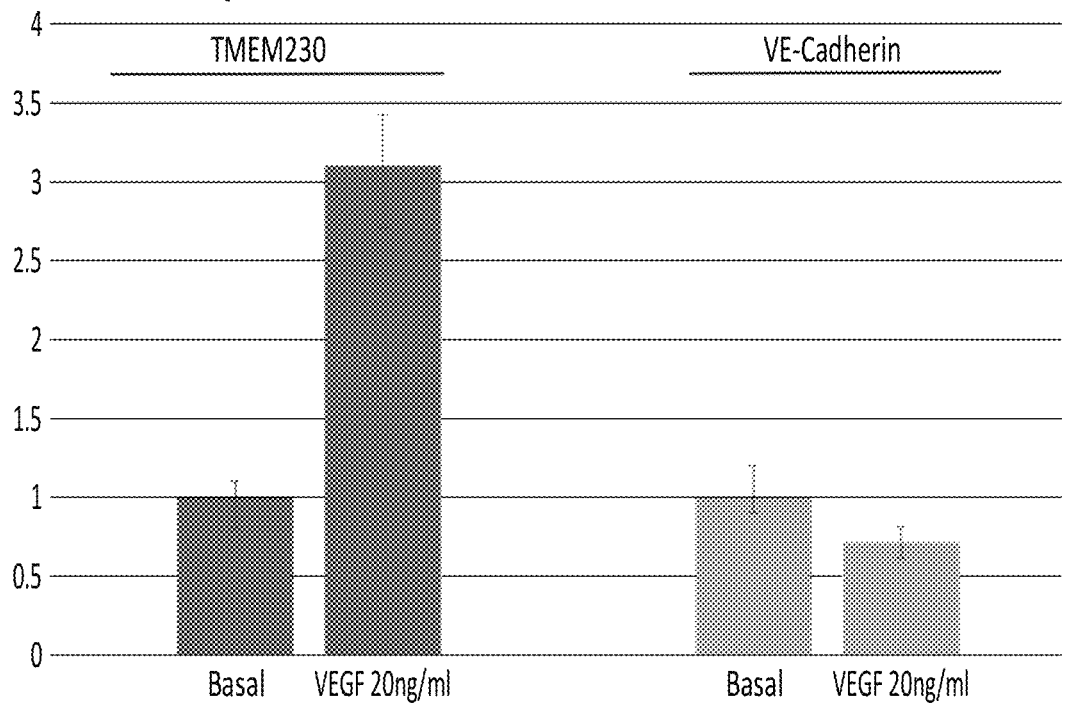

FIG. 12. Angiogenesis induced by VEGF is associated with inverse regulation of TMEM230 and of VE-cadherin in HUVEC cells. Quantitative PCR was used to evaluate the expression of TMEM230 and of E-cadherin in cells treated with VEGF and in untreated cells, demonstrating that VEGF induces underregulation of VE-cadherin and overregulation of TMEM230.

Figure 13:
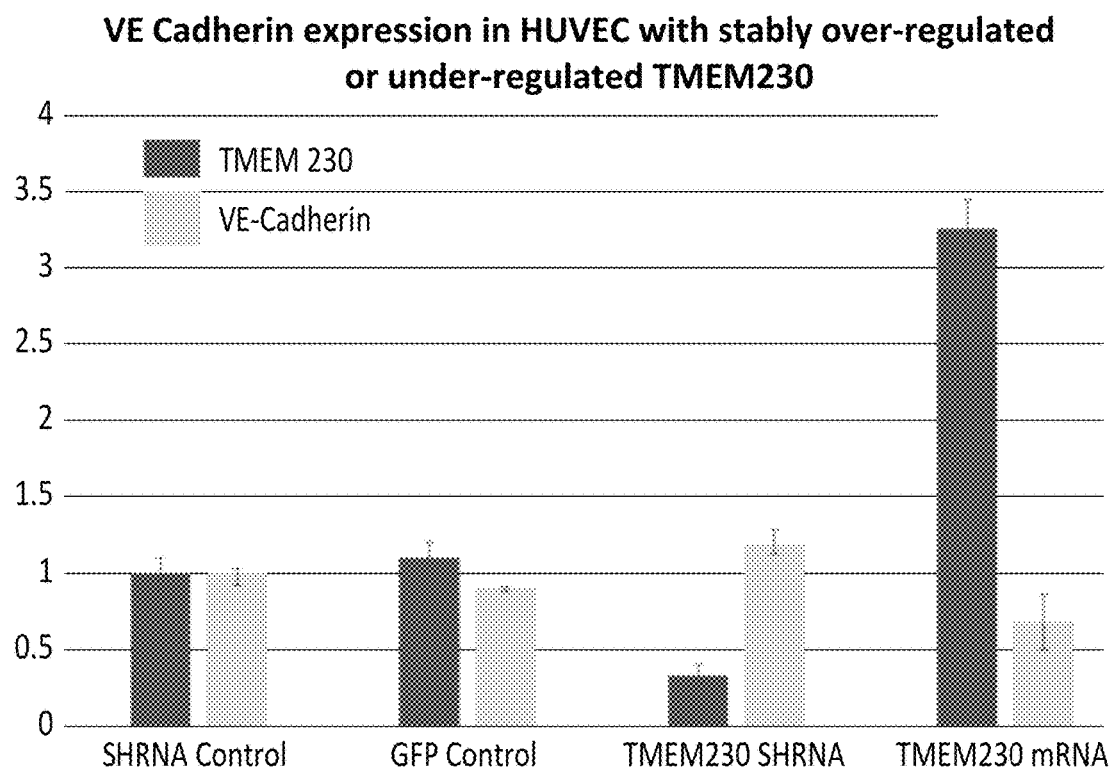

FIG. 13. Expression of VE-cadherin in HUVEC with TMEM230 overregulated or underregulated in a stable manner.

Figure 14:
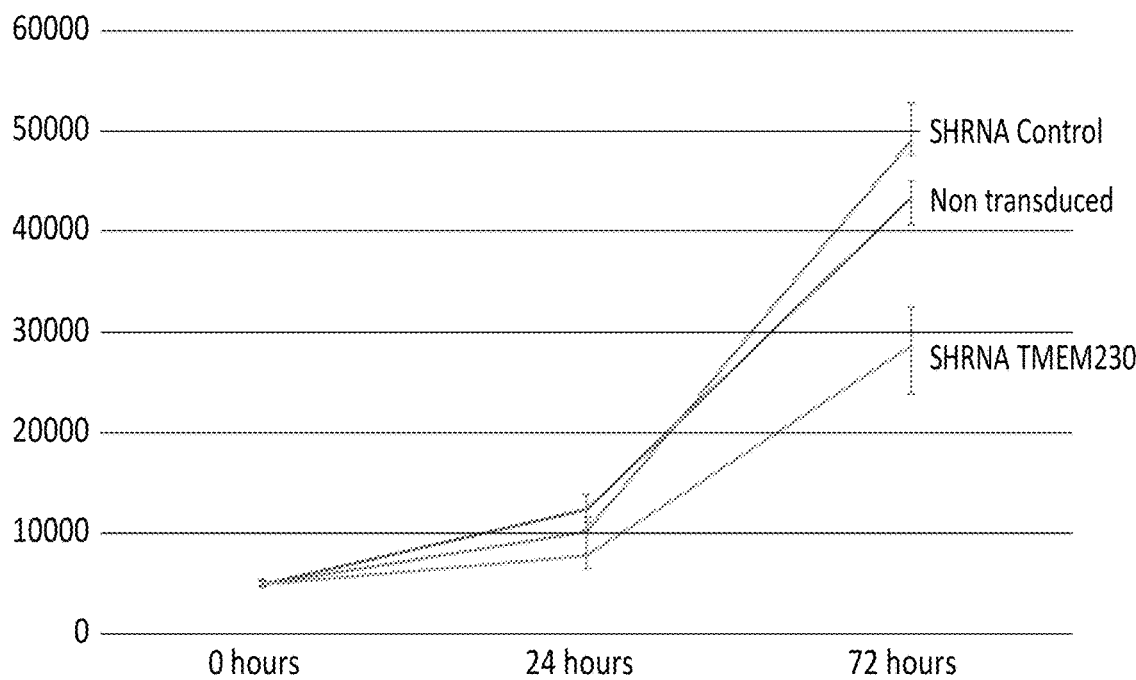

FIG. 14. The underregulation of the levels of expression of TMEM230 reduces the proliferation of HUVEC cells cultivated in growth-promoting conditions of adherence. A reduction of the number of cells is observed after reduction of the levels of expression of TMEM230 in the culture of HUVEC cells, showing that TMEM230, in addition to modulating sprouting and migration, could also play a role in proliferation.

Figure 15:
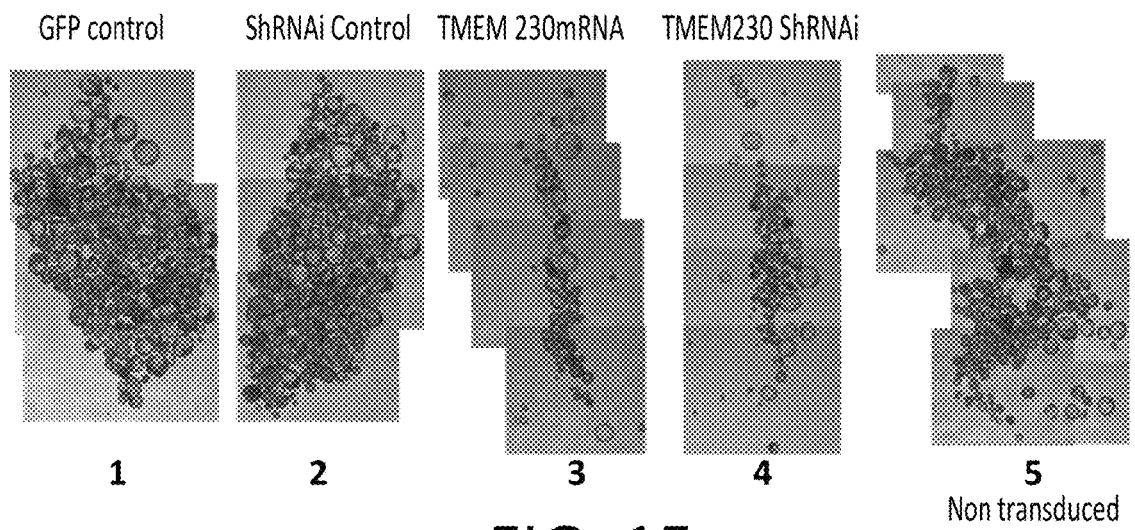

FIG. 15. Effect of the modulation of TMEM230 on the formation of acini produced by MCF7v. The constitutive overregulation of the TMEM230 transgene or the reduction of the TMEM230 protein native in MCF7 breast tumour cells indices a reduction of the formation of acini. The formation of cysts is a model for studying the formation of 3D and organoid structures.

Figure 16:
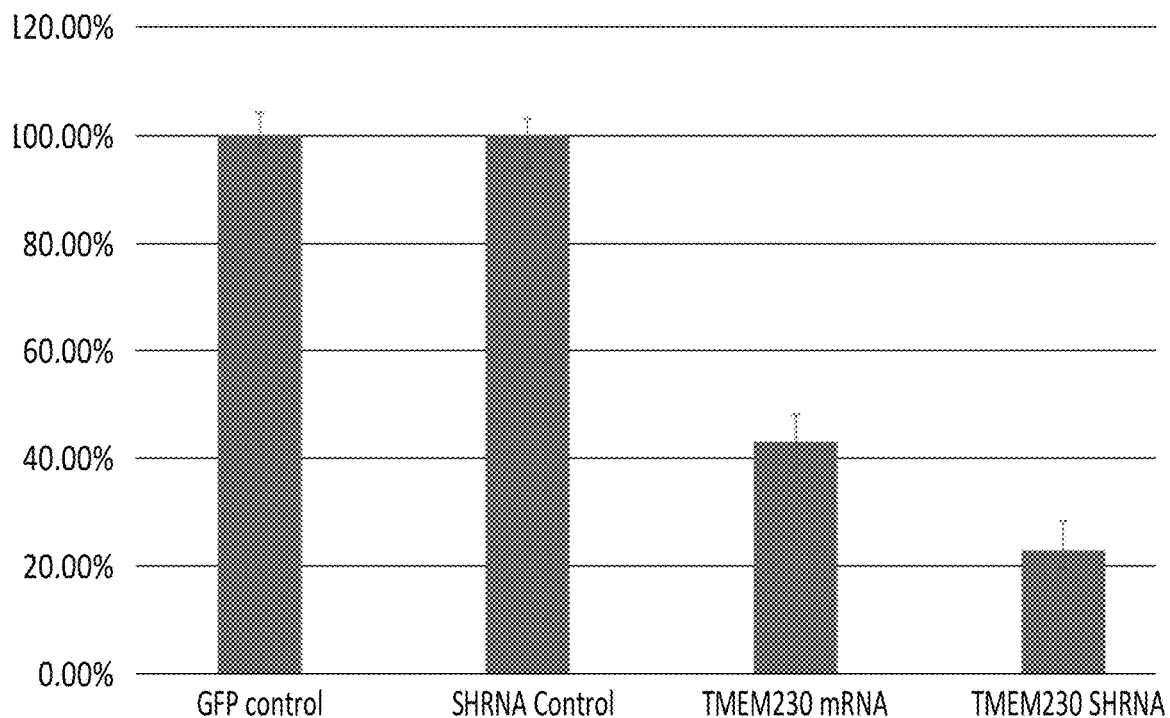

FIG. 16. Quantitative analysis of the number of acini formed by McF7v in the assay shown in FIG. 15. Quantitative analysis of the number of acini formed by MCF7v in which the levels of expression of TMEM230 were modulated in accordance with the assay described in FIG. 15.

Figure 17:
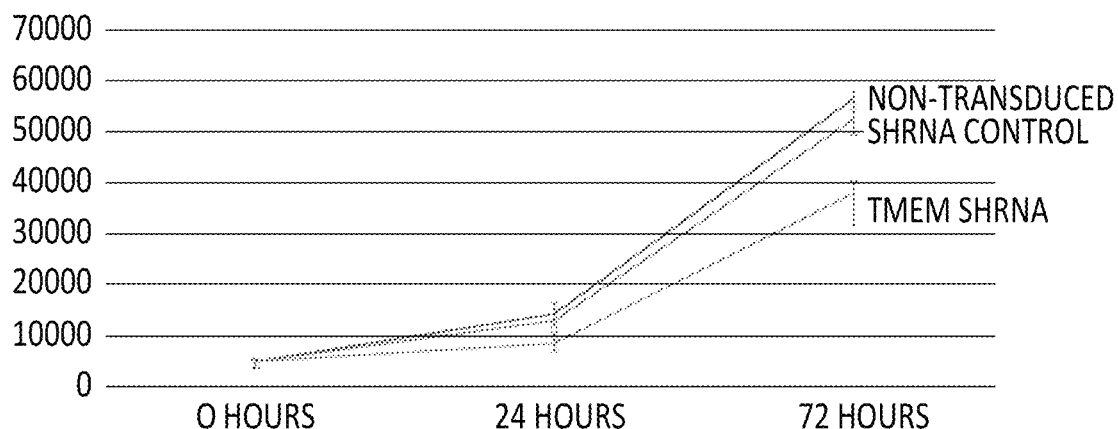

FIG. 17. The underregulation of TMEM230 comprises a reduction of the number of MCF7vcells grown in suspension. The cells obtained by the disassociation of the acini produced in FIG. 15 were counted. The reduction of the levels of TMEM230 comprises the generation of fewer and smaller acini.

Figure 18:
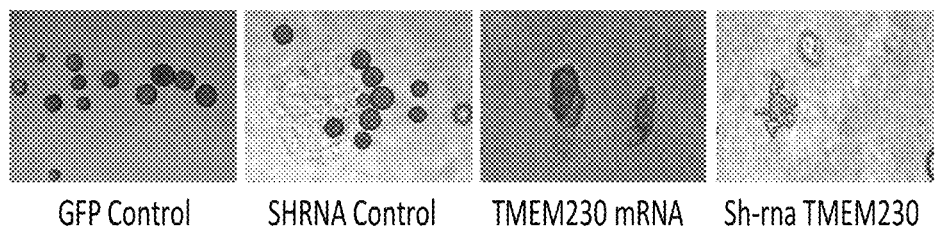

FIG. 18. The reduction of the levels of expression of the mRNA of TMEM230 in MCF7v translated into a reduction of the capability of the cells to form colonies in soft agar. Colonies produced by MCF7v in which TMEM230 was underregulated (sh-RNA TMEM230) or overregulated (TMEM230mRNA) compared to the controls.

Figure 19:
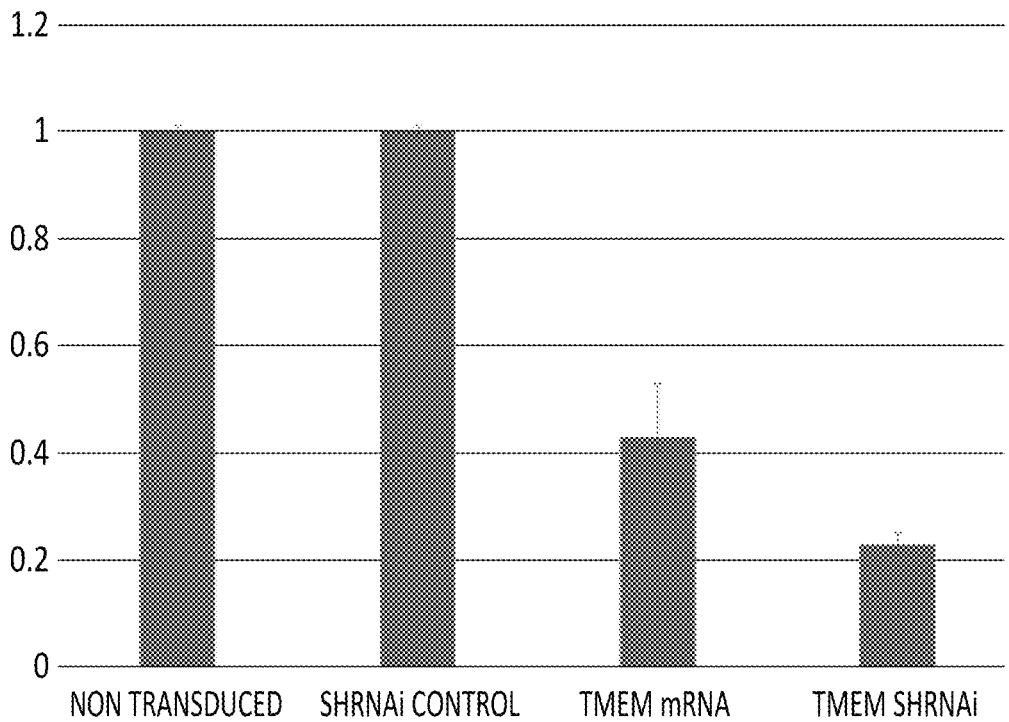

FIG. 19. Quantitative analysis of the number of colonies in soft agar generated by MCF7v.

Figure 20:
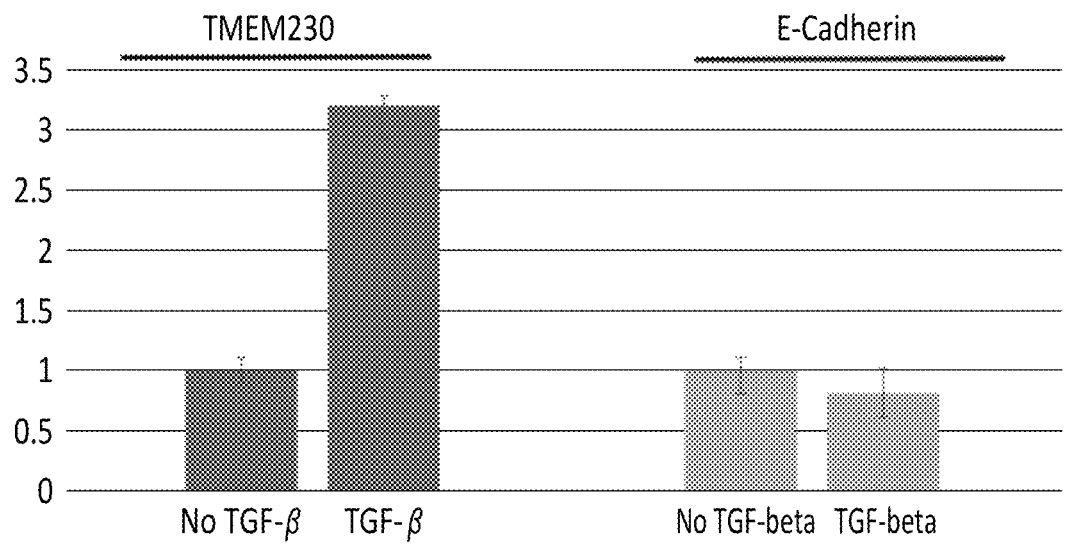

FIG. 20. Expression of TMEM230 and E-cadherin in MCF7v induced with TGF-beta.

Figure 21:
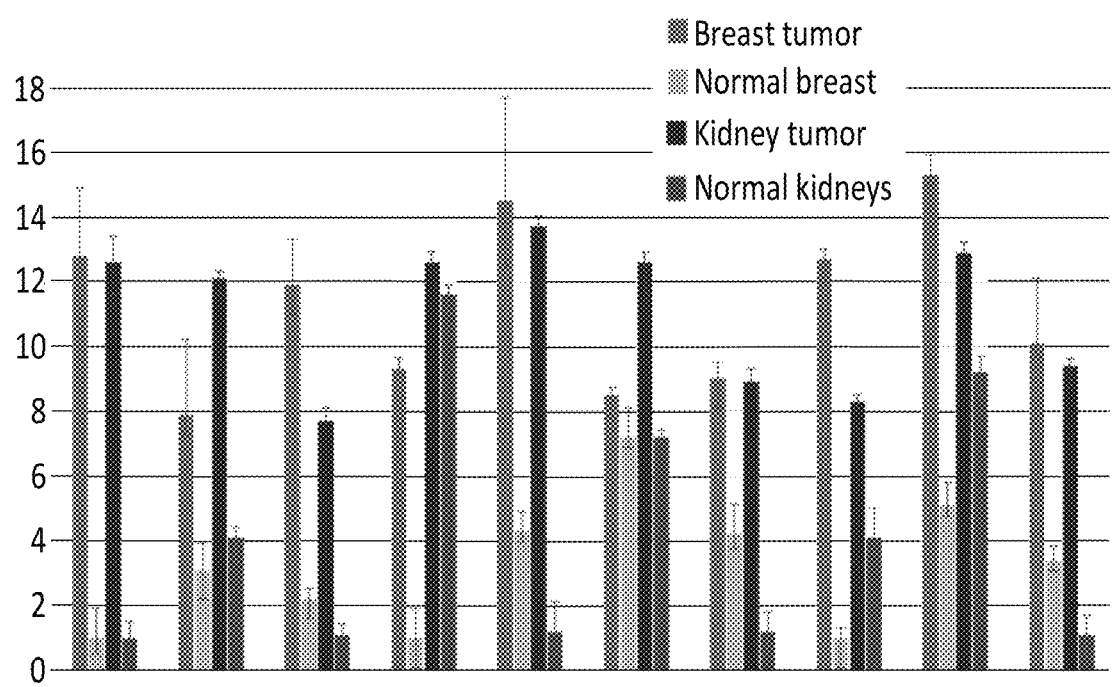

FIG. 21. Elevated expression of TMEM230 was observed in human tumour tissues compared to the healthy counterpart.

The assessment of the levels of expression of TMEM230 was performed in normal and tumoral human kidney and breast tissues by means of quantitative PCR. Since the normal functional blood vessels contain cells with low levels of TMEM230 and since the transient overexpression of TMEM230 in the endothelial cells promotes angiogenesis and germination of the endothelial cells, the elevated expression of TMEM230 observed in the human breast tumours and human kidney tumours could suggest that the tumour tissues contain more functional blood vessels compared to normal tissue.

Figure 22:
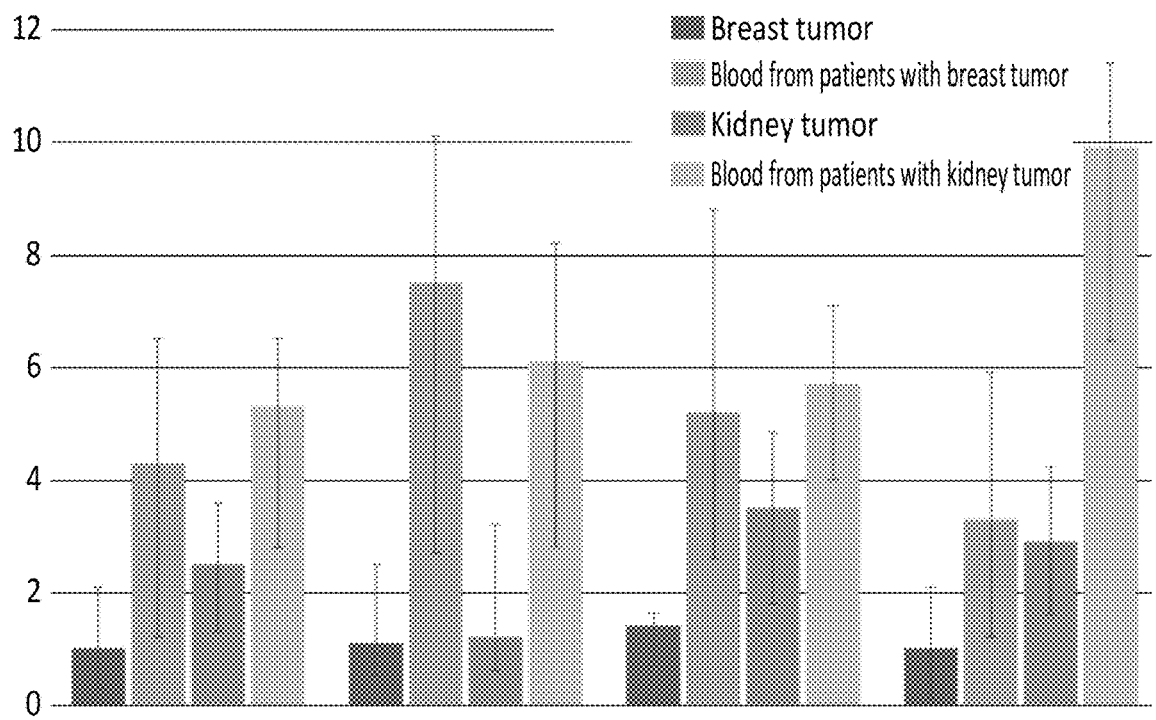

FIG. 22. Expression of TMEM230 in tumour blood cells.

Figure 23:
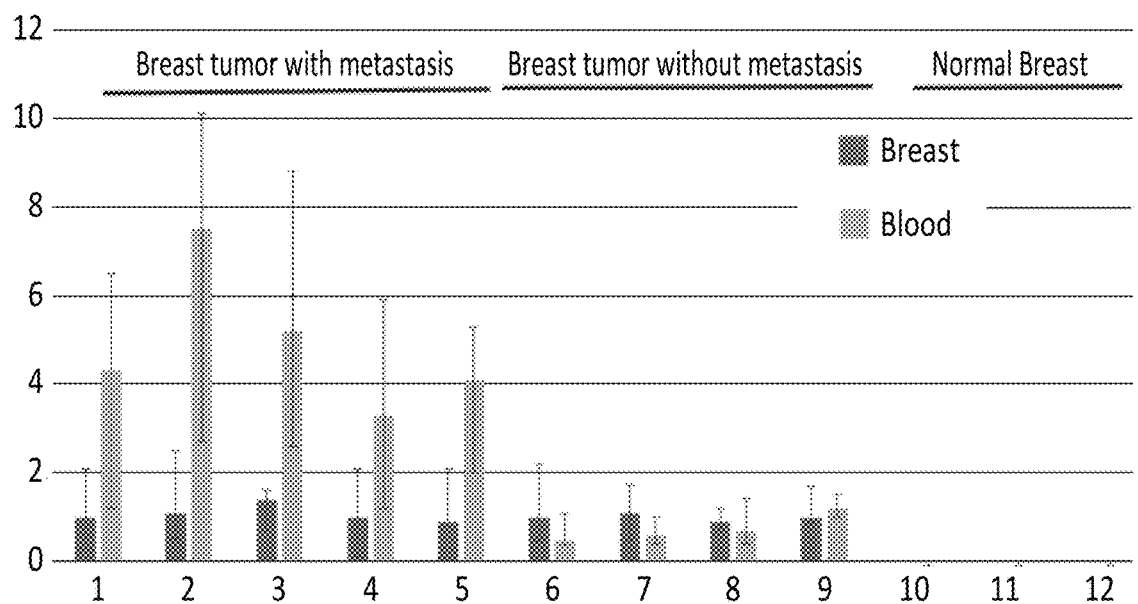

FIG. 23. The higher expression of TMEM230 in blood samples derived from patients with metastatic tumours compared to patients affected by tumours without metastases.

Human endothelial cells derived from patients and cultures of organotypic human epithelial cell cultures were used as in vitro models to modulate the levels of TMEM230 for the purpose of understanding the function thereof. When TMEM230 is overregulated, this promotes sprouting, migration, and invasion of the cells, these being functions necessary for the formation of 3D structures containing lumen (vessels, tubules, ducts, acini and alveoli), these being structures that are essential for the function of organs and tissues and for the branching thereof (branching morphogenesis). The controlled modulation of TMEM230 can play a therapeutic role in the treatment of diseases in which a therapeutic modulation of angiogenesis is necessary, in the treatment of tumours and in the prevention of metastases, and in regenerative medicine. When TMEM230 is underregulated, the epithelial-mesenchymal transition (EMT) is blocked, promoting the acquisition of an endo/epithelial-like phenotype, this being a property that is desirable in order to maintain functional vascular structures for the purpose of suppressing the dissemination of the tumour cells to organs distant from the site of origin of the tumour and for preventing the invasion and migration of the tumour cells and the neoangiogenesis induced by tumours. The research performed by the inventors suggests that the modulation of TMEM230 is necessary and sufficient to promote or inhibit angiogenesis in vitro and in vivo.

The ex situ cultures of endothelial and epithelial cells demonstrate that TMEM230, depending on its levels of expression, is able to induce or suppress endothelial sprouting and the formation of luminal, tubular, ductal and alveoli structures; the redundancy of the factors associated with the Notch/VEGF pathway and with the epithelial-mesenchymal transition mechanism are well characterised by means of ex situ and in vivo studies using primary human cell line tissues and the zebrafish model system demonstrate that the modulation of TMEM230 is necessary and sufficient to activate or suppress sprouting.

GLOSSARY

TMEM230. For the purposes of the present invention, TMEM230 means the human gene or any of the protein isoforms expressed by said gene as indicated in detail below.

The protein TMEM230 is coded by the gene TMEM230 which has ID 15876 in the HGNC database and ID: 29058 in the NCBI database.

In contrast to zebrafish, where the tmem230 protein is coded by 2 paralogous genes: tmem 230a, which maps to chromosome 10, and tmem230b, which maps to chromosome 8, these being distinguishable from one another by their sequence, in humans and in mice only a single gene codes for the protein TMEM230. In humans, the gene maps to chromosome 20 and gives rise to 9 variants produced from alternative splicing, generating 9 transcripts of different lengths, comprised between 1468 and 1754 nt. The 9 aforesaid splicing variants are formed by 5 exons assembled differently, more specifically 8 variants which all generate the same protein of 120 amino acids, coded by the 3 central exons (3-4-5), however these 8 mRNA have different lengths insofar as they include exons 1 and 2 in different combinations. The different lengths of the messengers are also caused by the presence of different portions of the 5' UTR, whereas the 3' UTR is equal for all 9 transcripts. A single splicing variant generates a protein of 183 aa, Access number: NP_001009923.1 GI: 58331120 183 aa protein coded by all 5 exons. The protein of 120 aa corresponds to 95% of the TMEM230 isoforms and is highly conserved.

For the purposes of the present invention, modulation/regulation of the activity of the TMEM230 protein means the modulation/regulation at DNA, RNA or protein level for all the isoforms expressed by the gene TMEM230 reported below.

The reference numbers for the gene and for all the currently known transcription variants that fall under the definition according to the present invention of "TMEM230" are therefore reported. For all of the sequences, reference is made, for the purposes of the present description, to those available in the databases with the provided reference numbers, as available to the public on the filing date of the present invention.

Gene TMEM230:
HGNC Official full name of the HGNC transmembrane protein: HGNC:15876 Ensembl: ENSG00000089063; HPRD:12762; Vega:OTTHUMG00000031796 also known as HSPC274; C20orf30; dJ1116H23.2.1

Transcripts Expected by TMEM230:
*Homo sapiens* transmembrane protein 230 (TMEM230) Access number: XM_011529229.1 GI: 768013713;
transcription variant X5, mRNA 1591 bp Access number: XM_011529228.1 GI: 768013708;
transcription variant X4, mRNA 1754 bp Access number: XM_006723561.2 GI: 768013705;
transcription variant X3, mRNA 1371 bp Access number: XM_011529227.1 GI: 768013703;

transcription variant X2, mRNA 1688 bp Access number: XM_005260713.2 GI: 768013700;
transcription variant X1, mRNA 1646 bp Access number: NM_001009925.1 GI: 58331123;
transcription variant 4, mRNA 1468 bp Access number: NM_001009924.1 GI: 58331121;
transcription variant 2, mRNA 1792 bp Access number: NM_001009923.1 GI: 58331119;
transcription variant 1, mRNA 1574 bp Access number: NM_014145.4 GI: 58331118;
transcription variant 3, mRNA 1699 bp.

EXPECTED TMEM230 PROTEIN: transmembrane protein 230 isoform X1 [Homo sapiens]
Access number: XP_011527531.1 GI: 768013714 120 aa protein
Access number: XP_011527530.1 GI: 768013709 120 aa protein
Access number: XP_011527529.1 GI: 768013704 120 aa protein
Access number: XP_006723624.1 GI: 578835403 120 aa protein
Access number: XP_005260770.1 GI: 530425717 120 aa protein
Access number: NP_001009925.1 GI: 58331124 120 aa protein
Access number: NP_001009924.1 GI: 58331122 120 aa protein
Access number: NP_001009923.1 GI: 58331120 183 aa protein Isoform 2 anticipated for transmembrane protein 230 [Homo sapiens] Access number: NP_054864.3 GI: 42476068 120 aa protein. To "modulate/regulate TMEM230" means to modulate and/or regulate the activity of transmembrane protein 230 (TMEM230) with regard to the expression of the gene coding for transmembrane protein 230, or at RNA or mRNA level of the TMEM230 gene or also at protein level of transmembrane protein 230, wherein this modulation can be both positive (thus increasing the activity of TMEM230 in tissues or in cells in which it is implemented) and negative (thus reducing the activity of TMEM230 in the tissues or in the cells in which it is implemented).

Agent that modulates/regulates the activity of TMEM230 for the purposes of the present invention means any molecule or compound able to exert a modulation of overregulation or underregulation of the activity of the transmembrane 230 protein, wherein this final overregulation or underregulation can be obtained by means of regulation at DNA level (expression), at RNA or mRNA level (transcription), or directly at protein level. For the purposes of the present invention, an agent that modulates/regulates the activity of TMEM230 is an agent that suppresses or increases the expression of the gene coding for TMEM230, an agent that acts at RNA or mRNA level of TMEM230, for example a miRNA, an siRNA, an shRNA, an iRNA or the like, or an agent that acts at TMEM230 protein level, influencing the activity thereof, for example inhibiting it (antibody or antibody fragment that binds TMEM230 in a specific way, that is to say binds only TMEM230 and does not bind other proteins, or indeed does not bind any isoform thereof in a specific way without binding the others), or increasing it, for example with mRNA which specifically produces the TMEM230 protein or with a mimetic peptide.

Sprouting: angiogenetic process caused by conditions of hypoxaemia, in which many parenchymal cells respond by secreting VEGF-A.

Tip cells: endothelial cells that emit filopodia, which grow longer towards the hypoxic zone digesting the extracellular matrix (ECM); tip cells entrain the other endothelial cells, which enter into a state of active proliferation.

Filopodia: Filaments emitted by the endothelium cells provided with receptors for VEGF-A which are modelled dependently of the VEGF-A gradient, being directed where it is more concentrated, opening up a gap through the matrix. They entrain the other endothelial cells.

Stalk cells. The cells that are not tip cells and that form the vessel.

```
SEQUENCE LISTING OF INHIBITORS OF TMEM230

SEQ ID 1: SASI_HS02_00305720
GAAACUAUAGCUGAGGACU[dT][dT]

SEQ ID 2: SASI_HS02_00305720 As
AGUCCUCAGCUAUAGUUUC[dT][dT]

SEQ ID 3: SASI_Hs02_00305721
GGUCCUUCCCAAAGAUGUU[dT][dT]

SEQ ID 4: SASI_Hs02_00305721 As
AACAUCUUUGGGAAGGACC[dT][dT]

SEQ ID 5: SASI_Hs01_00039897
GAUGUUAAGUGAACCUACA[dT][dT]

SEQ ID 6: SASI_Hs01_00039897 As
UGUAGGUUCACUUAACAUC[dT][dT])
```

DETAILED DESCRIPTION OF THE INVENTION

As mentioned in the summary above, the authors of the present invention have for the first time characterised the function of the TMEM230 gene in mammals and in animal models and also in fish (zebrafish) models. The characterisation of the activity of this gene has made it possible to identify a new therapeutic target for the treatment of pathologies that require angiogenesis regulation, in positive (induction of angiogenesis) or in negative (inhibition of angiogenesis).

The present invention therefore provides, for the first time, agents which modulate/regulate the activity of transmembrane protein 230 for use in treatment of pathologies in which angiogenesis regulation is necessary. Disclosed here for the first time is the concept of using agents which modulate/regulate the activity of the transmembrane protein 230 in the treatment of pathologies that require angiogenesis regulation in positive or negative for therapeutic purposes, more specifically diseases in which an induction or an inhibition of angiogenesis has a therapeutic effect on the progress of the disease. The term 'therapeutic effect' means that the modulation/regulation of the activity of TMEM230 induces a biological or medical response in an animal or human tissue system, which response is desired by a researcher, veterinarian, general medical practitioner or other clinical doctor, including the alleviation of the symptoms of the disease or of the disorder that is to be treated.

In one embodiment of the invention, such agents modulate/regulate the activity of the human transmembrane protein 230, whereas, in other embodiments, such agents can exert their modulation/regulation on the expression of homologues or paralogues of said protein in other mammals.

The term 'agent that modulates/regulates the activity of the transmembrane protein 230' as indicated above, for the purposes of the present invention, means any molecule or compound able to exert a modulation on the expression, transcription, or translation of the gene TMEM230, its RNA, its mRNA, or at protein level that results in an overregulation or underregulation of the activity of the transmembrane protein 230 (TMEM230) as defined above by means of the above-indicated sequences.

In other words, in accordance with the invention, the agent that modulates/regulates the activity of TMEM230 can be any pharmacologically acceptable agent able to modulate the activity of TMEM230 acting at DNA, RNA, mRNA, or protein level.

For the purposes of the present invention, an agent that modulates/regulates the activity of TMEM230 can be selected from: an agent that suppresses or increases the expression of the gene coding for TMEM230, an agent (regulator) which acts at RNA or mRNA level of TMEM230, or an agent (regulator) which acts at TMEM230 protein level.

In one embodiment of the invention, the agent that modulates/regulates the activity of TMEM230 is an agent that regulates the expression, transcription, or translation of the gene TMEM230. Non-limiting examples of agents which suppress or increase the expression of the gene TMEM230 can be an agent that activates the promoter of the gene, an agent that inhibits the promoter of the gene, and the like.

Alternatively, the agent that modulates/regulates the activity of the transmembrane protein 230 (TMEM230) according to the invention can be an RNA or mRNA inhibitor selected from miRNA, shRNA and siRNA oligonucleotides, optionally chemically modified and having a sequence complementary at least in part to the mRNA sequence coding for the membrane protein TMEM230.

Numerous miRNAs have been presented in the literature that can inhibit TMEM230 for example at mRNA level, wherein non-limiting examples include miR134 ID entry 406924, miR-181 ID entry 406955, miR-200 ID entry 406983 and miR-203 ID entry 406986.

In a non-limiting embodiment of the invention, possible oligonucleotides for reducing the expression of TMEM230 and therefore for exerting a modulation that lowers the levels of said protein can be used in the form of one or more pairs of oligonucleotides having, respectively, SEQ ID NOS: 1-2, 3-4, 5-6 as reported in the list of sequences.

In any case, for this purpose, double-stranded RNA oligos contained in the mRNA sequence of human TMEM230 can be used to breakdown the TMEM230 messenger. According to standard techniques, oligos are then "annealed" in accordance with the protocol in laboratory use in accordance with which, for example, each single strand is incubated at a concentration of approximately 20 mM, in a suitable buffer, such as a buffer containing 100 mM of potassium acetate, 30 mM of HEPES-KOH at pH 7.4, and 2 mM of magnesium acetate, for the necessary time at elevated temperature, for example for 1 minute at 90° C., then the oligos are held for approximately one hour at approximately 37° C.

The mRNA sequence of the gene TMEM230 being known, available also in its possible variants in the public databases (access numbers reported above and below), a person skilled in the art will be able to easily design antisense shRNA or siRNA oligonucleotides or find miRNA in databases by means of standard techniques using programs available to the public (Targetscan, Pictar, Miranda, DIANA) or acquiring these nucleotides from companies specialised in this field.

A person skilled in the art will be able to design various oligonucleotides suitable for carrying out the invention, on the basis of his common general knowledge in the art. The modifications commonly used in the prior art for example include modifications to the sugar of the nucleotide, modifications to the nucleic base, and modifications to the internucleotide bond.

As known to a person skilled in the art, oligonucleotides for RNA inhibition, and therefore also the siRNAs and the shRNAs, can be chemically modified in various ways known to a person skilled in the art and can also be designed and produced as commercial products by specialist providers (for example the companies Ribotask, Riboxx Life Sciences, Dharmacon GE Healthcare, Exiqon, miRIDIAN Hairpin inhibitor design; Dharmacon Products, Thermo Fisher Scientific). Examples of chemical modifications that can be applied to RNA inhibitor oligonucleotides and that do not limit the present invention include one or more of the following modifications: conjugation at the 3' position of the oligonucleotide to cholesterol; use in the construction of the oligonucleotide of locked nucleic acid (LA), that is to say a bicyclic analogue of RNA in which the ribose is blocked in a C3'endo confirmation by means of introduction of a 2'-O, 4'-C methylene bridge; use of nucleotides modified at the 2' position of the ribose molecule, such as 2'-fluoro (2'-F), 2'-O-methoxyethyl (2'-O-MOE), 2'-O-methyl (2'-O-Me); use of nucleotides modified by substitution of the ribose with a 6-element morpholino ring; use of nucleotides with phosphorothioate bond (PS linkage) modified by means of substitution of one of the oxygen atoms in the phosphate group (not forming part of the bond) with a sulphur atom, as shown in the schemas below.

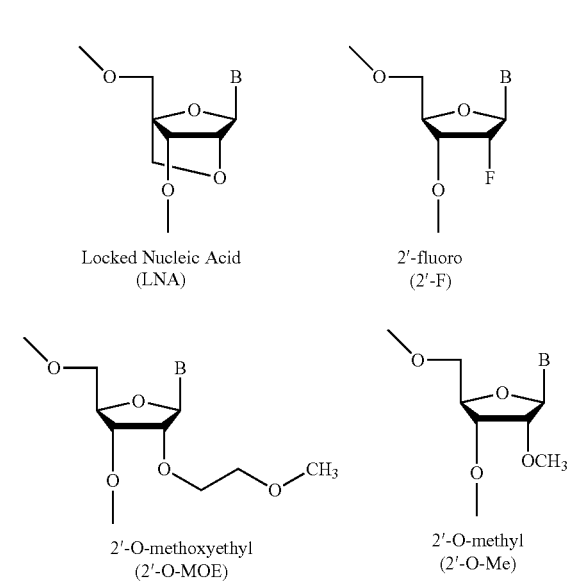

Locked Nucleic Acid (LNA)

2'-fluoro (2'-F)

2'-O-methoxyethyl (2'-O-MOE)

2'-O-methyl (2'-O-Me)

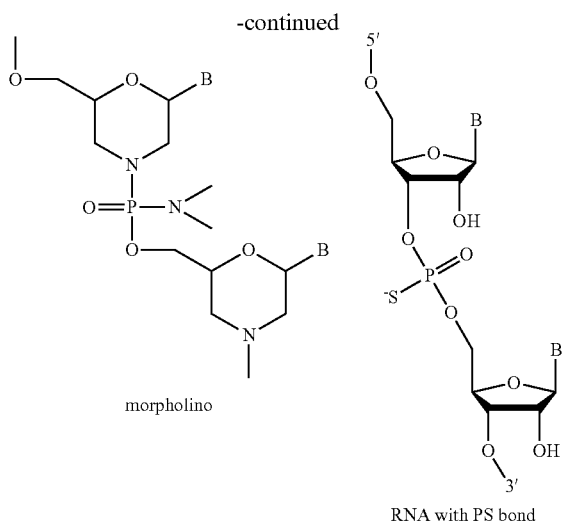

morpholino

RNA with PS bond

As known to a person skilled in the art, the above-mentioned chemical modifications can also be combined in the same oligonucleotide; for example, inhibitors that have more modifications can be provided, such as oligonucleotides conjugated to cholesterol at the 3' position, the nucleotides of which are 2'-O-MOE nucleotides, or oligonucleotides that contain 2'-O-MOE nucleotides and 2'F nucleotides, or oligonucleotides that contain LMA nucleotides and deoxyribonucleic acid (DNA), also short oligonucleotides (for example formed by the sequence complementary to the seed sequence) formed by LNA nucleotides, in which the above-listed combinations can have PO bonds also PS bonds and other combinations. In one embodiment of the present invention, agents which modulate/regulate the activity of the protein TMEM230 can therefore be used which act on the expression of the protein TMEM230 at RNA or mRNA level, formed from oligonucleotides having a sequence complementary to the mRNA coding the transmembrane protein 230 as reported in the available databases, for example access number: XM_011529229.1 GI: 768013713; access number: XM_011529228.1 GI: 768013708; access number: XM_006723561.2 GI: 768013705; access number: XM_011529227.1 GI: 768013703; access number: XM_005260713.2 GI: 768013700; access number: NM_001009925.1 GI: 58331123; access number: NM_001009924.1 GI: 58331121 access number: NM_001009923.1 GI: 58331119 access number: NM_014145.4 GI: 58331118), where NN and XM are the NCBI access numbers, and GI is an acronym for GENE ID, or to part thereof, wherein said oligonucleotides can be chemically modified by one or more of the chemical modifications described above.

In other words, the agent of the present invention which modulates/regulates the activity of the protein TMEM230 acting on the expression of TMEM230, inhibiting its RNA or mRNA, is preferably represented by an oligonucleotide as defined above, comprising one or more chemical modifications selected from the group represented by one or more modified internucleosidic bonds, one or more modified or substituted ribose molecules, one or more modified bases, or a binding to a carrier molecule, for example conjugation with a cholesterol molecule.

In one embodiment, said internucleosidic bonds can be phosphorothioate bonds (PS) as defined above, said modified ribose molecules can be molecules in which the ribose is locked into a C3'-endo confirmation by introduction of a 2'-O, 4'-C methylene bridge; use of nucleotides modified in position 2' of the ribose molecule, such as 2'-fluoro (2'-F), 2'-O-methoxyethyl (2'-O-MOE), 2'-O-methyl (2'-O-Me); said substituted ribose molecules being able to be substituted by a 6-element morpholino ring.

The modifications mentioned above are some of the most common modifications known to a person skilled in the art of interfering RNAs (therefore for use as inhibitors), however it is clear that other commonly used modifications should also be considered as included within the embodiments of the present invention.

As mentioned above, modifications of this kind have the objective of increasing the affinity of the agent of the invention with the target RNA, of increasing its bioavailability in vivo, of increasing its resistance to degradation, and of increasing its stability in duplex form, therefore when bound to target RNA and the like.

A person skilled in the art, on the basis of the information provided here and standard protocols, will be able to easily provide inhibitory oligonucleotides specific for the RNA or mRNA coding the protein TMEM230 (which therefore hybridise only with said RNA or mRNA) as defined above. Methods and programs which make it possible to evaluate the specificity of said oligonucleotides are also available, and for example include programs commonly used by a person skilled in the art in order to evaluate the possible cross-linking and therefore the specificity of antimiR, such as BLAST, Vmatch, and RNAhybrid. The CrossLink program, for example, can be used to evaluate potential interactions between the oligonucleotides for inhibition of mRNA and its target sequence.

In a further embodiment of the present invention, the agent that modulates/regulates the expression of TMEM230 can be an agent that modulates the activity of the transmembrane protein 230 and can be selected from an antibody or an antibody fragment which binds the protein TMEM230 in a selective manner, or a bioactive peptide, more specifically modulates the activity of TMEM230, which for example can mimic the activity of the protein TMEM230, or can act with a negative dominant effect, inhibiting the function of said protein.

With regard to the antibodies, numerous suitable antibodies are commercially available, for example, but not exclusively, from Life Span BioSciences, Atlas Antibodies, Origene, Santa Cruz Biotechnology, Aviva Systems Biology, AbcaM, Novus Biologicals, Abnova Corporation, United States Biological, GeneTex.

In accordance with the present invention, the pathologies in which angiogenesis regulation is necessary are pathologies in which positive or negative regulation of angiogenesis has a therapeutic effect which reduces, alleviates, or eliminates the symptoms of the disease or of the disorder that is to be treated.

Pathologies of this kind can be pathologies in which an increase or a reduction of angiogenesis results in a therapeutic effect, for example, but without limitation, ischaemia induced by vascular disorders and occurring in diseases such as diabetes, arterial insufficiency, peripheral artery disease, stroke, vascular degeneration induced by ageing, macular degeneration, chronic inflammation including rheumatoid arthritis, Crohn's disease, psoriasis, endometriosis, lower extremity arterial disease, deep vein thrombosis, Raynaud's phenomenon, chronic occlusive arterial disease, vascular ulcers, diabetic retinopathy and all vascular complications of diabetes including diabetic foot arterial disease, thrombosis of the retinal arteries, acute vascular trauma, myocardial ischaemia, ischaemic damage to the myocardium, infarcted heart ischaemia, occlusive diseases of cerebral arteries and cerebral ischaemic infarction, arteriosclerotic dementia linked to the vasculature, advanced-stage solid tumours, early-stage solid tumours, and other pathologies known to a person skilled in the art that would benefit from an induction of angiogenesis.

In accordance with the invention, such pathologies can be treated by providing a transient overregulation of the activity of the protein TMEM230 which can be obtained by means of agents which positively modulate/regulate (stimulate) the expression of said protein at DNA, RNA or mRNA level or which act directly at protein level as described herein, followed by a negative regulation of the activity of the protein which, depending on the circumstances, can be obtained by means of the suspension of the treatment inducing the stimulus or by means of the administration of agents which negatively modulate (suppress) the expression of TMEM230 at DNA, RNA or mRNA level or its activity at protein level as described herein.

Positive Modulation of Angiogenesis.

In cases of damage to the vascular tissue, when positive modulation of angiogenesis is required, the induction of angiogenesis can be obtained using combinations of modulator/regulator agents administered in sequence: the first increases levels of expression of TMEM230 to induce sprouting and proliferation of the endothelial cells, and the second reduces said expression levels to promote reconstitution of the walls of the vessels and complete the process of angiogenesis. For the positive modulation according to the invention, agents which act positively on the expression of the protein or repeated transfections of mRNA of TMEM230 can be used.

RNA can be produced synthetically by specialised companies, or can be prepared in a laboratory by generation of constructs ad hoc for the expression of the cDNA of interest. Such vectors are provided with the specific sequences of the promoters T7 or SP6 that allow transcription in vitro of the sequence of the cDNA cloned therein. The messenger of interest must be synthesised with high efficiency, and the messenger produced is easily purified in accordance with routine protocols.

In one embodiment, the agents according to the invention can therefore be used to induce angiogenesis. In this case, in accordance with the invention, an agent that positively modulates/regulates the activity of TMEM230 is used in a first phase, positively regulating the expression of the protein TMEM230 (at DNA, RNA, mRNA or protein level), this being following by a second phase, in which an agent that negatively modulates/regulates the activity of TMEM230 (at DNA, RNA, mRNA or protein level) is used. The agents according to the invention used as described induce angiogenesis and have a therapeutic effect in pathologies selected from chronic diseases that cause damage to the vascular tissue, such as in the case of the above-cited pathologies, or in lower extremity arterial disease, deep vein thrombosis, Raynaud's phenomenon, chronic occlusive arterial disease, vascular ulcers, diabetic retinopathy, and all the vascular complications of diabetes including diabetic foot arterial disease, thrombosis of the retinal arteries, acute vascular traumas, myocardial ischaemia, ischaemic damage to the myocardium, infarcted heart ischaemia, occlusive diseases of cerebral arteries and cerebral ischaemic infarction, cerebrovascular disease, arteriosclerotic dementia linked to the vasculature.

Negative Modulation of Angiogenesis.

In accordance with the present invention, the pathologies in which an increase of angiogenesis exacerbates the symptoms of the disease and accelerates the progression thereof, such as in the case of chronic inflammation, including rheumatoid arthritis, Crohn's disease, diabetic retinopathy, psoriasis, endometriosis or early-stage solid tumours, and in all pathologies in which the negative modulation of angiogenesis is therapeutic, an agent that negatively modulates/regulates the activity of TMEM230 (thus reducing it) is useful.

Depending on the severity of the pathology and the level of the inhibition, the inhibition of angiogenesis can also be provided by means of agents that promote the overregulation of the levels of expression of TMEM230.

In one embodiment, the agents according to the invention are used to inhibit angiogenesis and to destroy blood vessels. In this embodiment, said agent that modulates/regulates the activity of TMEM230 at DNA, RNA, mRNA or protein level is an agent as described herein which modulates said activity positively, promoting the destruction of the vessels and the inhibition of angiogenesis.

Inhibition of Tumoral Angiogenesis.

In accordance with a further embodiment, the pathologies in which negative regulation of angiogenesis is necessary include solid tumours. The authors of the present invention have found that, with regard to early-stage solid tumours, a reduction of the levels of expression of TMEM230 (and therefore a negative regulation) that results, as described above, in an inhibition of the sprouting (FIG. 4) is sufficient. In fact, in the early stages of the formation of a tumour (initial tumour), a transient reduction of the expression of TMEM230 is necessary in order to block neoangiogenesis (preventing formation of tip cells and branching of new blood vessels) and in order to prevent the migration of tumour cells, preventing said cells from invading and reaching the bloodstream (FIG. 4C, box a).

The regulator/modulator that reduces the activity of TMEM230 in this case can therefore be used in anti-cancer therapies as an anti-metastatic anti-angiogenic agent. In all the embodiments of the invention, the term 'circulating tumour cells' includes stem tumour cells.

In the advanced stages of a tumour a negative regulation of angiogenesis directed at the destruction of the vessel system feeding it is clearly therapeutic. The authors suggest the overexpression of TMEM230, which induces destabilisation of the capillaries that supply the tumour, thus leading to a subsequent reduction of the tumour mass due to an absence of nutrients. At the same time, the formation of metastases is blocked because the epithelial cells are unable to enter the compromised circulatory network.

The tumours against which the regulation of TMEM230 can have a therapeutic effect, in the early stage by means of a reduction of the expression, or in the advanced stage by means of an increase of the expression of said protein, including invasive tumours originating from transformed cells of mesenchymal origin: bone, cartilage, muscles, vessels; invasive tumours originating from transformed cells of epithelial/ectodermal origin: cancer of the breast, colon, kidney, prostate, liver, thyroid, ovary, brain and lung.

In all of the above-mentioned embodiments, transient regulation methods are preferred.

The invention also relates to a pharmaceutical composition for use in the treatment of pathologies in which angiogenesis regulation is necessary, comprising one or more agents which modulate/regulate TMEM230 activity (at DNA, RNA, mRNA or protein level as described above) as defined in any one of the embodiments described above and at least one pharmaceutically acceptable carrier.

A person skilled in the art will be able to define the temperature and times, the dosages and excipients necessary depending on the selected administration method and the pathology to be treated.

Manuals for the preparation of pharmaceutical compositions are available in the literature and can be easily consulted by a person skilled in the art in order to select the excipients necessary for the preparation of pharmaceutical compositions comprising, as active ingredient, one or more modulators according to the invention.

The invention also relates to a pharmaceutical composition or a pharmaceutical kit for sequential use in the treatment of pathologies in which a regulation of angiogenesis is necessary, comprising at least one vial containing at least one therapeutic dose of an agent that positively modulates/regulates TMEM230 activity (at DNA, RNA, mRNA or protein level as described above), thus resulting in an increase in the activity of the transmembrane protein 230 protein and at least one vial containing at least one therapeutic dosage of an agent that negatively modulates/regulates TMEM230 activity (at DNA, RNA, mRNA or protein level as described above), thus resulting in a reduction of the activity of the transmembrane protein 230 membrane, wherein said pathology is a tumour and the agents are as defined above.

Lastly, the invention relates to a therapeutic method for the treatment of pathologies in which angiogenesis regulation is necessary, as defined above, comprising the step of administering, to a human subject in need thereof, an agent that modulates/regulates TMEM230 activity (at DNA, RNA mRNA or protein level as described above) as described above.

That described above in relation to the agents according to the invention, the modulation methods, and pathologies also applies to the therapeutic method forming a further subject of the invention.

Since the authors of the invention have demonstrated that TMEM230, in addition to a therapeutic target, is also a marker of metastasis that is detectable in blood or plasma, the invention also relates to a method for the diagnosis of metastasis in patients suffering from cancer, comprising the step of quantifying the expression of TMEM230 in a sample of blood or serum of a patient suffering from cancer comparing the expression of TMEM230 in said sample to the one detected in a control sample representative of the TMEM230 expression values in blood or serum of a healthy individual wherein, when the expression of TMEM230 in the patient sample analysed is equal to at least 2 times, preferably 4 times, preferably 6 times the expression of TMEM230 in the control sample, this corresponds to the presence of metastases and/or circulating cancerous cells or metastatic cells in said patient.

The method described here can of course also be included in a therapeutic method in which the diagnosis of the presence of circulating cancerous cells or metastatic cells can allow a treatment tailored to the patient, wherein the doctor can choose the most suitable therapy based on the type of cancer, the age, sex, weight and overall state of health of the patient. The therapy can include treatments by means of regulation of the expression of TMEM230, optionally in combination with conventional antitumour treatments.

The invention therefore also relates to a kit for the diagnosis of circulating tumour cells or metastatic cells in patients suffering from cancer, comprising one or more reagents for the quantification of TMEM230 in serum or blood samples, one or more control samples representing the values of TMEM230 expression in blood or serum of a healthy individual. The control sample can be represented by sera from healthy individuals or by solutions in which TMEM230 (in the form of nucleic acid or protein or parts thereof) can be calibrated so as to have a concentration equal to that detectable in a pool of healthy samples.

The reagents for TMEM230 detection can be any one of the reagents described in the present description depending on whether the detection is performed at nucleic acid or protein level.

The following examples are intended to illustrate the scientific basis of the invention.

EXPERIMENTAL EXAMPLES

Zebrafish as a Model for Discovering the Function of TMEM230.

Although in a recent study it was reported that the gene TMEM230 was found to be mutated in patients suffering from Parkinson's disease, the function of the gene TMEM230 has not been described previously, and therefore, the inventors have, for the first time, studied the function of the gene during embryonic development, using zebrafish (*Danio rerio*) as in vivo model and human tissues and cell lines derived from patients or continuous lines as in vitro models.

The zebrafish model is an ideal system because, compared to the mouse model, it has a unique combination of characteristics that make it particularly suitable for use as a model for genetic and functional studies relating to the development of vertebrates, wherein in recent years numerous methodologies making it possible to exploit all of the advantages thereof have been developed and perfected. Zebrafish from a single fertilised egg, which quickly develops to adult stage, and therefore genes that regulate the initial development of organs and tissues can be studied in zebrafish within a period of days, and therefore the transitory modulation of the expression of a gene of interest can be easily mediated from siRNA oligos rather than from transgenic technologies, which, being based on the genomic integration of an exogenous DNA, could result in the deregulation of other genes and could be harmful. In addition, the formation of organs and tissues and of the defects imparted thereto by the underregulation of a specific gene can be easily, continuously and directly visualised thanks to the fact that the zebrafish is transparent in the early phases of development. At 24 hours after fertilisation (hpf herein for 'hours post fertilisation'), the embryos show almost all the tissues and the precursors of many organs already formed, each of which can be easily observed with use of a simple transmission microscope (Weinstein 2002). The microinjection of antisense oligonucleotides, referred to as morpholinos (MOs), has proven to be useful in order to study in vivo the function of a gene by means of the specific inhibition of its translation or by modifying the splicing events experienced by the pre-mRNA (Ekker 2000; Nasevicius and Ekker 2000; Kole and Sazani 2001). The use of zebrafish also makes it possible to perform loss of function tests of 2 genes simultaneously, injecting 2 different MOs and reversing the phenotype obtained by injecting one of the two MOs in combination with the mRNA of the other gene. The transparency and accessibility of the embryos of zebrafish make it possible to efficiently apply experimental methods also by in vivo analysis of the vascular development (Weinstein, Stemple et al. 1995). Thanks to the reduced dimensions of the embryos of zebrafish, they receive sufficient oxygen to survive by passive diffusion from the external media and continue to develop normally for a number of days, even in a complete absence of blood circulation, thus allowing phenotype analysis even in cases in which circulatory defects have proven to be lethal in other organisms (Stainier 2001). These characteristics have made it possible to perform screenings of mutants on a large scale for the purpose of isolating embryonic mutations that are detrimental to the cardiovascular system and/or nervous system, resulting in models of various human diseases (Driever, Solnica-Krezel et al. 1996; Haffter, Granato et al. 1996).

In order to determine TMEM230 function, the inventors have therefore carried out initial studies using the zebrafish model and the zebrafish gene zgc:101123 (genbank BC080236) orthologous to the Tmem230 gene expressed in mammals. The gene zgc:101123 codes for a protein of which the alignment with the TMEM230 human and mouse proteins has shown, respectively, 76% identity and 88% similarity. The analyses in the genome database have shown that 2 tmem230 genes are present in the zebrafish genome: tmem230a (zgc:101123) on chromosome 10 and tmem230b (zgc:162251) on chromosome 8 (FIG. 6, section A). The two genes code for proteins that are closely related to one another and that in fact have high percentages of identity and similarity (83% and 93% respectively, section B). Using quantitative PCR, the temporal expression of both genes during the phases of early embryonic and larval development in zebrafish and in adult organs and tissues was evaluated, and it was demonstrated that the transcripts are expressed in all analysed stages of development, from the first phases of segmentation up to 120 hpf. The expression both of Tmem230a and Tmem203b in all analysed adult organs (brain, eyes, gills, digestive system, heart, liver and muscle) was also confirmed. Whole-mount analysis of the expression by means of in situ hybridisation revealed that, from the stage of late somitogenesis at 26 hpf, Tmem230a is mainly expressed in the developing vascular system (section C) compared to Tmem230b, and therefore the study of the characterisation of the function of the gene was performed exclusively for Tmem230a and the role identified forms the subject of the present patent.

In order to analyse the role of Tmem230a during zebrafish development, the inventors performed loss of function tests, separately injecting 2 different morpholino oligos. The morpholino Tmem230a-MO (MO1) designed to block translation of Tmem230a, and a splicing-blocking morpholino (MO2) designed straddling the exon2/intron2 junction which leads to the production of an aberrant messenger, devoid of exon 2. Since the injection of the splicing-blocking morphilino oligo MO2 produces results qualitatively similar to those obtained following the injection of the morpholino MO1, the study was performed using MO1, and the term "morphant" denotes the zebrafish embryos injected with said oligo at a dose of 0.3 pmol/embryo. At this dose, MO1 does not cause any significant defects in the morphology or circulation in the injected embryos.

In order to confirm the role of Tmem230a at vascular system level, the pattern of expression of vascular markers was analysed in the morphants and in the control embryos at 29 hpf. At this stage of development, vasculogenesis is finished, blood circulation and angiogenic sprouting of the arterial intersomitic vessels (aISVs) have begun, and the arterial intersomitic vessels are formed by 3 or 4 endothelial cells with separate positional destinies (Isogai Lawson et al. 2003). A T-shaped tip cell is positioned further dorsally and contributes to the formation of the dorsal longitudinal anastomotic vessel (DLAV), a connection cell located halfway along the somite and a basal cell that connects to the dorsal aorta. At 29 hpf, expression of ephrin-B2 and its receptor ephB4, specifically expressed respectively at the arterial and venous endothelium, and expression of 3 markers specific to tip cells: flk1, receptor 2 of vegf; flt4 receptor 3 of vegf; and dII4 Notch delta-like 4 ligand; were analysed (Fouquet, Weinstein et al. 1997) (Wang 1998; Adams, Wilkinson et al. 1999; Gerety, Wang et al. 1999) (Shutter, Scully et al. 2000; Siekmann and Lawson 2007). (Thompson, Ransom et al. 1998).

The expression of such markers in tip cells in the morphants Tmem230a was higher than in control embryos (83% n=57; 79% n=52; 53% n=44 respectively). These results show that Tmem230a has a key role in the determination of the arterial-venous destiny and in controlling the behaviour of the cells during angiogenesis.

Conclusion 1.

The initial studies in zebrafish have demonstrated that 1) the TMEM230 gene and protein are conserved in vertebrates, 2) in zebrafish the expression of Tmem230a is necessary to maintain normal function of the blood vessels, and 3) the function of the Tmem230 protein is that of regulating sprouting, that is to say germination of endothelium cells (FIG. 6).

In order to quantify the number of ISA cells, the inventors thus used zebrafish embryos obtained from a transgenic line in which Green Fluorescent Protein (EGFP) under the control of the promoter of the vascular gene fli1 (tg(fli1: nEGFP)$^{y7}$ (Roman, Pham et al. 2002) has a nuclear localisation, making it possible to visualise the cells forming the arterial intersomitic vessels which appear green under fluorescence microscope. The number of endothelial cells forming the first 10 aISVs in the Tmem230a morphants at 29 hpf revealed a statistically significant increase in the number of cells forming the aISVs compared to the controls (FIG. 6, section A, box b), similarly to that observed by Siekmann and Lawson following the loss of function of dII4 after injection of the morpholino against dII4 (dII4-MO) (Siekmann and Lawson 2007). In order to evaluate whether there is a synergy between Tmem230 and dII4 in the induction of the rise in the number of cells forming the aISVs, morpholino against Tmem230a and against dII4 were injected at low doses. Whereas injections independent of the 2 morpholinos at low doses did not cause any changes to the number of cells forming the aISVs in the injected embryos (not shown in FIG. 3), co-injections thereof at low doses resulted in a significant rise in the number of cells that form the aISVs, as observed in the double morphants compared to the controls and the single morphants (FIG. 6, section B, box c). In addition, the injection of Tmem230a mRNA in embryos injected with dII4-MO re-established the normal number of endothelial cells at aISV level (Section B, box d), suggesting that Tmem230 mRNA is able to reverse the phenotype caused by the down-regulation of dII4 obtained by injection of dII4-MO (box b). In subsequent experiments, the inventors also blocked Notch signalling using the inhibitor of γ secretase, DAPT (Geling, Steiner et al. 2002) and demonstrated that the embryos treated with DAPT present an increase in the number of cells of the aISVs compared to the control embryos. The embryos injected with Tmem230a mRNA and then treated with DAPT presented a number of cells forming the aISVs comparable to the number of cells counted in the control embryos (experiment not shown), indicating that Tmem230a mRNA is also able to reverse the phenotype caused by DAPT.

During angiogenesis, various signals guide an endothelial cell and direct it towards tip or stalk behaviour. Tip cells express the receptors Vegfa (Vegfr-2) and Vegfc (Vegfr-3/Flt4). Vegfa induces, in tip cells, the expression of dII4, Notch ligand, and the activation of Notch inhibits tip behaviour in stalk cells, in part, inhibiting the expression of flt4 (Gerhardt, Golding et al. 2003; Covassin 2006; Siekmann and Lawson 2007; Tammela, Zarkada et al. 2008). It has been demonstrated that embryos of zebrafish, similarly to those of mice, in which dII4 is inhibited, demonstrate an excessive branching of vessels and excessive endothelial proliferation that can be normalised, reducing Vegfr-3/flt4 signalling (Siekmann and Lawson 2007; Tammela, Zarkada et al. 2008; Hogan 2009) Hellstrom 2007; Siekmann and Lawson 2007). Based on these results, the inventors co-injected Tmem230a-MO both with vegfc-MO and with flt4-MO, separately and together. The embryos injected only with morpholino vegfc-MO (FIG. 6, Section C, box c) or only with morpholino vegfc-MO (Section C, box e), show a reduced number of cells of the alSVs compared to the controls (box a), and compared to the embryos injected with Tmem230a-MO (MO1) (the number of the endothelia of the alSVs) (box b). Conversely, the co-injection of Tmem230a-MO (MO1) with the morpholino against vegfc (box d) and with the morpholino against flt4 (box f), in both conditions, results in a recovery of the phenotype. This result also summarises the results obtained following the co-injection of the morpholino dII4-MO and of the morpholino vegfc/flt4, described by Hogan and colleagues (2009) and by Siekmann and Lawson on Rbpsuh-deficient embryos (Siekmann and Lawson 2007).

Conclusion 2.

The loss of function tests heavily indicate that in zebrafish, in the absence of Tmem230a, the endothelial cells exhibit tip cell behaviour, resulting in an increase in the number of endothelial cells forming the arterial intersomitic vessels. Such results are similar to those obtained in embryos injected with the morpholino dII4-MO, in fact in the absence of dII4/notch signalling all the endothelial cells become cells of the tip type. Similarly, when Notch signalling is blocked by the inhibitor of the γ secretase, DAPT, the embryos present a rise in the number of cells in the alSVs. In both cases, the injection of the Tmem230a mRNA leads to the recovery of the normal phenotype. In addition, the injection of the morpholino Tmem230a-MO reverses the phenotype obtained following the injection of the morpholino vegfc-MO and of the morpholino flt4-MO, reproducing the results obtained from the experiments with injection of dII4-MO.

Since the loss or underregulation of Tmem230 mRNA induces tip behaviour in the cells and promotes the formation of new blood vessels, recapitulating the scenario previously observed in embryos in which the dII4/Notch signalling has been inhibited, the inventors suggest that in zebrafish Tmem230 is involved in the specification of the identity of the cells forming the intersomitic vessels and that it acts as a master regulator of factors that control Notch signalling during the germination of the endothelial cells.

Studies with Model Systems Based on Human Cells.

Given that the TMEM230 gene is evolutionarily conserved and the Notch pathway regulates many types of cells, the inventors have hypothesised that, insofar as it is a regulator of the Notch signalling path, TMEM230 should be associated with other types of cells and have taken into consideration various cell types and different species, including man. To identify the role of TMEM230 in human cells, the levels of the RNA and protein TMEM230 were firstly determined in endothelial cells and in normal epithelial cells and tumour cells isolated from patients and in cell lines. In accordance with the results obtained in zebrafish, the expression of the TMEM230 protein was identified in HUVEC cells (endothelial cells of the human embryonic umbilical vein) used in vitro as a model for identifying factors that regulate the formation of the vessels in the neo processes or angiogenesis in man (FIG. 7). Cultures of HUVEC in 3D recapitulate the initial steps associated with the process of neoangiogenesis and were used as a model to study branching and morphogenesis of endothelial vessels. In order to evaluate the role of TMEM230 in HUVEC cells, conditional lentiviral constructs were produced and used to increase or reduce the levels of TMEM230 expression. TMEM230 repression was obtained by constructs with the antisense sequences (SIRNA) that breakdown TMEM230 mRNA, whereas the overregulation of TMEM230 was obtained by cloning TMEM230 mRNA in the same vectors (FIGS. 8 and 9).

TMEM230 Modulation in Human Endothelial Cells.

The zebrafish experiments demonstrated that with the overregulation of Tmem230 obtained from the application of the morpholino, the number of cells in the intersegmental region of the dorsal aorta increased. The rise in the number of cells could be interpreted as a rise in the real proliferation, understood to be a cell produced from a mother cell, or could be the result of a change in the morphology of one cell into another, that is to say a change from a cell that does not have migratory features into a cell able to migrate. The inventors have therefore developed similar tests using human endothelial cells derived from the umbilical cord (HUVEC) and have demonstrated that in three-dimensional (3D) cultures, the overregulation of TMEM230 causes the cells to acquire migratory capability (FIG. 10). The inventors have therefore hypothesised that high levels of TMEM230 demolish cell-cell contacts and promote the acquisition of invasive and migratory behaviour, whereas the loss of TMEM230, achieved by reduction of the levels of the TMEM230 messenger, induces maintenance of the epithelial phenotype and of cell-cell contacts.

The inventors have also observed that the underregulation of TMEM230 in HUVEC cells cultivated in 3D seems to be able to induce early cell death, which suggests that the reduction of the TMEM230 levels could induce cell death by anoikis. The loss or underregulation of TMEM230 can therefore provide a therapeutic approach for targeting circulating tumour cells demonstrating high survival and thus elevated resistance to anoikis, in inhospitable conditions, such as conditions of hypoxia, in the blood or in the lymphatic vessels.

The inventors have therefore designed and constructed lentiviral vectors for overexpression of the TMEM230 human protein or for underregulation thereof, and have demonstrated that, in accordance with the results obtained using the zebrafish model system, the modulation of the expression of TMEM230 is necessary and sufficient to activate or suppress the sprouting induced by VEGF in HUVEC cells.

3D cultures in vitro in which sprouting and migration were induced by VEGF in the presence of TMEM230 basal levels or in the presence of overregulated or underregulated TMEM230 have shown that TMEM230, when underregulated, reduces sprouting and migration induced by VEGF (FIG. 10F), whereas, when overregulated, it has an additive effect with VEGF in the regulation of sprouting (FIG. 10B) compared to the controls.

The underregulation of TMEM230 produces inhibition of the sprouting induced by VEGF, supporting the idea that TMEM230 can be used as a target for the design of drugs for therapies of the pro/anti-angiogenic type and in antitumour therapy on account of its ability to inhibit neoangiogenesis. The inhibition of the formation of new vessels is the essential key to preventing the flow of oxygen and nutrients to the tumour and therefore for stopping the growth thereof. Moreover, inhibiting the formation of vessels and preventing the vessels from reaching and permeating the tumour mass means that the invasive tumour cells will not have access to the systemic circulation, and therefore they will not be able to reach sites far from the site of origin and give rise to the formation of secondary tumours (FIG. 4C).

In conclusion, the study of TMEM230 modulation in HUVEC cells has demonstrated that TMEM230, when overregulated, promotes migration and sprouting of the endothelial cells cooperating with VEGF in a synergistic way, whereas in the absence of VEGF the overregulation of TMEM230 induces sprouting and migration in a VEGF-independent manner (FIG. 10D).

Given that the TMEM230 overregulation is sufficient to encourage and recapitulate angiogenic sprouting in basal medium, independently of the induction with VEGF (FIG. 10D), the authors have evaluated whether the expression of TMEM230 was overregulated in endothelial cells after induction with VEGF. Analyses of quantitative expression (RT-PCR) have shown that the induction of angiogenic sprouting and migration dependent on VEGF are associated with TMEM230 overregulation (FIG. 12) and that TMEM230 is an integral part of the regulatory network of angiogenesis.

This data supports the hypothesis that TMEM230 is sufficient to induce the first step associated with angiogenesis and could be crucial when VEGF or other pro-angiogenic factors are absent or non-functional due to mutations or due to modifications of the epigenomic type.

In conclusion, TMEM230 is a target for the design of drugs and its modulation could be useful in the control of angiogenesis and in regenerative medicine.

The reduction of the number of proliferating cells observed with the repression of TMEM230 expression in HUVEC cells stimulated with VEGF suggests that TMEM230, in addition to promoting sprouting and migration, depending on its level of expression, could also play a role in the control of cell proliferation.

Since the induction of new blood vessels is fundamental for the preservation of the tumour mass and for promoting tumour growth, and since it has been demonstrated that in tumours there is a rise in the density of the functional blood vessels, which have the role of supporting tumour mass growth with nutrient substances and oxygen (FIG. 4A), angiogenesis inhibition has recently revealed itself to be one of the most promising therapeutic strategies for implementing a blocking of tumour progression and preventing the formation of metastases. The inventors have thus evaluated TMEM230 expression in human breast tumours and in the healthy counterpart and observed higher levels of TMEM230 mRNA in tumour tissues compared to normal tissues (FIG. 21).

TMEM230 Modulation in Breast Epithelial Cells.

Given that the gene TMEM230 can both inhibit and promote angiogenesis and the formation of blood vessels, the inventors propose TMEM230 also as a potential target gene for antitumour and anti-metastasis therapies and suggest that, in order to inhibit the formation of new blood vessels in early tumours, TMEM230 should be kept at low levels in the endothelial cells (FIG. 4C, box a). By contrast, in order to disassemble the existing blood vessels and interrupt the cell-cell contacts in a tumour mass at advanced stage, TMEM230 must be temporarily overregulated (box b) and alternate cycles of overregulation and underregulation could increase the efficacy of the treatment.

Given that a marked overexpression of TMEM230 was observed in human breast and kidney tumours and in normal and tumoral human cell lines (FIG. 21) in order to study the role of TMEM230 in the regulation of pathways associated with invasion and EMT, a sub-clone derived in a laboratory of MCF7 (cell line isolated from invasive breast tissue) was used. The cells of the clone MCF7v, when cultivated in 3D suspension conditions, generate acini (organoids that recapitulate the structures that form during the terminal differentiation of the breast epithelial cells from pregnancy) and undergo morphological changes similar to the EMT transition after treatment with TGFbeta.

To determine if TMEM230 modulation promotes or suppresses the formation of organoid structures, TMEM230 was overexpressed and underexpressed compared to the controls, in which TMEM230 was expressed at basal level. Both the overregulation and underregulation of TMEM230 in MCF7v cultivated in 3D liquid conditions led to the formation of a smaller number of acini compared to the control (FIG. 15).

The reduction in the number of acini observed with TMEM230 overexpression could be attributed to the reduction of E-cadherin (CDH1) expression, which promotes the loss of cell-cell junctions, similarly to that observed with TMEM230 overexpression in HUVEC cells (FIG. 12). In addition, given that TGFbeta promotes EMT transition, with subsequent loss of the intracellular junctions and concurrent E-cadherin underregulation, an analysis of mRNA expression was performed in MCF7v after treatment with TGFbeta. It was observed that the treatment with TGFbeta induces TMEM230 overregulation (FIG. 20) and that the treatment with TGFbeta or TMEM230 overexpression, induced by transduction of the lentiviral construct expressing TMEM230, provoke E-cadherin underregulation (FIG. 13). Since the formation of acini requires a perfect morphology of epithelial type with well defined and strictly regulated apical and basolateral polarity, the reduction of the formation of acini could be due to the E-cadherin underregulation and to the subsequent inability of the cells to maintain stable cell-cell contacts.

To validate the hypothesis that the reduction of the TMEM230 levels induces the loss of resistance to anoikis, observed in the experiments with the endothelial cells, TMEM230 was underregulated in the MCF7v cells, cultivated in suspension. The underregulation of TMEM230 shows a significant rise in cell death, confirming the initial hypothesis. The inventors have also demonstrated that also in MCF7v cultivated in conditions of adherence, the downregulation of TMEM230 induces a decrease in the number of cells that can be associated with an inhibition of the proliferation and/or vitality of the cells.

Since the treatment with TGFbeta of the MCF7v cells provokes TMEM230 overregulation, this suggests that TMEM230 is a component of the TGFbeta pathway and that TMEM230 is essential for inducing the EMT-like transition, necessary for the migration and invasion of luminal cells.

The invasive behaviour was tested using luminal cells derived from human breast gland which have the ability to form colonies in soft agar. The overexpression of the TMEM230 transgene leads to the acquisition of sprouting behaviour on the part of the cells (FIG. 18), as observed in the HUVEC cells (FIG. 10B).

In contrast, TMEM230 underregulation in the breast epithelial cells that form organoids induced a repression of the sprouting, again as already observed in the HUVEC cells (FIG. 10H). The inhibition of the EMT behaviour in the tumour cells is essential to suppress the formation of metastases in patients suffering from tumours. Since high levels of TMEM230 in the HUVEC cells and in the epithelial tumour cells derived from patients induce the cells to acquire invasive and migratory behaviour, reducing such levels, or preventing high levels of expression from being reached, could inhibit the ability to form metastases, firstly preventing the formation of new vessels and secondly preventing the epithelial tumour cells from acquiring invasive behaviour, necessary in order to reach the circulatory system (FIG. 4B).

The reduction of the ability to form acini following the underregulation of TMEM230 in the MCF7v cells could be caused also by an inhibition of the proliferation or by the greater susceptibility of the cells to anoikis-dependent cell death. In agreement with this, it was observed that the number of cells in the acini that form in the experiments in suspension was lower in the conditions in which TMEM230 was underregulated compared to the controls (FIG. 19). The MCF7 cells in which TMEM230 was underregulated were cultivated in conditions that promote the formation of colonies in soft agar, forming fewer and smaller colonies, in agreement with the observation that TMEM230 underregulation promotes a reduction in the proliferation and increases the susceptibility to anoikis-dependent cell death.

The reduction of the number of colonies in soft agar and the reduction of the number of acini in suspension suggests that the repression of TMEM230 expression could inhibit the dissemination of the cells to other loci and thus inhibit the formation of metastatic tumour at sites far from the site of origin.

In order to determine whether patients with breast tumours have high levels of TMEM230 in the blood, quantitative PCR was performed on a series of blood samples obtained from patients with breast and kidney neoplasia. TMEM230 was significantly increased (10 times) in the tumour samples compared to healthy controls.

Conclusion 3.

In conclusion, since TMEM230 was found to be overregulated in breast tumours and kidney tumours compared to the healthy counterpart of the same patient and overregulated in patients who had been diagnosed with metastasis, the authors suggest that high levels of TMEM230 expression in tumour samples could indicate that the level of TMEM230 expression could be correlated with a high density of blood cells in the tumour, or with a greater number of epithelial tumour cells in the tumour compared to the healthy control. In addition, high levels of TMEM230 in the tumour could suggest that TMEM230 could induce specific tumour properties, such as the migration and sprouting or invasion capabilities.

Patients diagnosed with metastatic breast tumours revealed elevated levels of TMEM230 in the tumour mass and in the blood compared to patients who had not been diagnosed with metastasis (FIG. 23). High blood levels of TMEM230 suggest that TMEM230 could be associated with circulating tumour cells and/or endothelial cells with high levels of TMEM230 expression or with fragments of cells derived from epithelial and/or endothelial cells with high TMEM230. Circulating cells were isolated by FACS from the blood of patients with neoplasia using the EPCAM marker. The circulating endothelial cells or cell fragments were easily derived from sprouting and/or from damaged or destroyed cells of the vascular system associated with the tumour.

Collectively, these results show that the underregulation of TMEM230 can represent a therapeutic approach for targeting tumour stem cells or circulating tumour cells and can lead them to destruction, countering their resistance to anoikis, and that TMEM230 can be used as a tumour marker for detection, prognosis and diagnosis, and could be a marker of diagnostic and prognostic value for the staging of the tumour and the evaluation of the risk of formation of metastases.

TMEM230 overregulation can be required in a specific localised area of the tumour, such that an overregulation of the protein can be targeted and non-generalised so as to prevent TMEM230 overexpression in tumour cells from provoking an acquisition by said cells of an invasive state. For example, the blood vessels at a certain distance from the tumour mass can be targeted by the TMEM230 overregulation and therefore their specific destruction, whereas blood vessels within the tumour mass will not be the target of the TMEM230 overregulation. Instead it would be sufficient to interrupt and destroy the capability of said cells to circulate outside the tumour mass.

In addition, delivery techniques exist that make it possible to specifically target specific blood cells which direct TMEM230 overregulation, avoiding other normal or tumoral epithelial cells. For example, a vector antibody that binds specifically to membrane proteins of the endothelial cells can carry an agent that specifically induces pharmacological TMEM230 overregulation in endothelial cells that delimit the tumour mass. The application of such techniques is included within the embodiments of the present invention.

In compliance with Article 170bis (2) of the Italian Industrial Property Code and in accordance with Article 21 (2) of the Implementing Regulation of the Italian Industrial Property Code adopted with Ministerial Decree 13.1.2010 no. 33 and in compliance with Article 170bis (2) of the Italian Industrial Property Code, and also Article 5 (3) of 10 Jan. 2006, no. 3 converted with modifications from the law of 22 Feb. 2009, no. 78, and in compliance with Article 22 (5) of the Implementing Regulation of the Italian Industrial Property Code adopted with Ministerial Decree 13.1.201 no. 33:

it is declared that:

the cell material described by way of example in the present application is of human origin and that the tissue cells described in the present application do not form part of the subject of the invention, were obtained from tumour tissue samples of patients in accordance with medical research principles as stipulated by the Hospital Ethics Committee, with the sample being taken after obtaining the free and informed signed consent of the patients.

The invention claimed is:

1. A method of treating a patient having a solid tumor that has not yet developed its own network of capillaries, which would sustain the solid tumor's growth and expansion, comprising administering an agent that negatively modulates or regulates activity of TMEM230 protein to the patient in need thereof to inhibit neoangiogenesis of the solid tumor and its metastasis; wherein said agent is an RNA inhibitor selected from one or more oligonucleotides comprising SEQ ID NOS: 1-2, 3-4 or 5-6.

2. The method according to claim 1, wherein said RNA inhibitor is selected from the group consisting of shRNA oligonucleotides and siRNA oligonucleotides with their nucleotides chemically modified and having a sequence complementary to at least part of the mRNA sequence coding for the TMEM230 protein.

3. The method according to claim 2, wherein said RNA inhibitor contains chemically modified nucleotides having one or more chemical modifications selected from the group consisting of: one or more modified internucleosidic bonds, one or more modified or substituted ribose molecules, and one or more modified bases.

4. The method according to claim 3, wherein said chemically modified nucleotides have one or more phosphorothioate internucleosidic bonds (PS).

5. A method of regulating angiogenesis according to claim 1, wherein the patient is administered a pharmaceutical composition comprising said agent that negatively modulates or regulates the activity of TMEM230 protein and at least one pharmaceutically acceptable carrier.

6. A method of regulating angiogenesis comprising administering an agent that negatively modulates or regulates activity of TMEM230 protein to a patient having a solid tumor that has not yet developed its own network of capillaries such that its development is inhibited and migration of tumor cells from the solid tumor to the subject's bloodstream is blocked; wherein said agent is an RNA inhibitor selected from the group consisting of shRNA oligonucleotides and siRNA oligonucleotides having a sequence complementary to at least part of the mRNA sequence coding for the TMEM230 protein; and said agent is selected from one or more oligonucleotides comprising SEQ ID NOS: 1-2, 3-4 or 5-6.

7. The method according to claim 6, wherein the patient is administered a pharmaceutical composition comprising said agent that negatively modulates or regulates the activity of TMEM230 protein and at least one pharmaceutically acceptable carrier.

8. The method according to claim 3, wherein said chemically modified nucleotides have one or more modified ribose molecules in which the ribose is locked into a C3'-endo conformation by introduction of a 2'-O, 4'-C methylene bridge (LNA nucleotides).

9. The method according to claim 3, wherein said chemically modified nucleotides have one or more modified ribose molecules in which the ribose is modified in position 2' with one of the following modifications: 2'-fluoro (2'-F), 2'-O-methoxyethyl (2'-O-MOE), or 2'-O-methyl (2'-O-Me).

10. The method according to claim 3, wherein said chemically modified nucleotides have one or more substituted ribose molecules in which the ribose is substituted by a 6-element morpholino ring.

* * * * *